United States Patent
Wang et al.

(10) Patent No.: US 10,539,689 B1
(45) Date of Patent: Jan. 21, 2020

(54) SPECTRAL X-RAY DETECTORS WITH DYNAMIC ELECTRONIC CONTROL AND COMPUTATIONAL METHODS

(71) Applicant: RENSSELAER POLYTECHNIC INSTITUTE, Troy, NY (US)

(72) Inventors: Ge Wang, Loudonville, NY (US); Wenxiang Cong, Albany, NY (US); Zaifeng Shi, Tianjin (CN)

(73) Assignee: Rensselaer Polytechnic Institute, Troy, NY (US)

(*) Notice: Subject to any disclaimer, the term of this patent is extended or adjusted under 35 U.S.C. 154(b) by 246 days.

(21) Appl. No.: 15/545,623

(22) PCT Filed: Jan. 25, 2016

(86) PCT No.: PCT/US2016/014769
§ 371 (c)(1),
(2) Date: Jul. 21, 2017

(87) PCT Pub. No.: WO2016/118960
PCT Pub. Date: Jul. 28, 2016

Related U.S. Application Data

(60) Provisional application No. 62/107,036, filed on Jan. 23, 2015, provisional application No. 62/150,887, filed on Apr. 22, 2015.

(51) Int. Cl.
*G01T 1/24* (2006.01)
*A61B 6/00* (2006.01)
*A61B 6/03* (2006.01)

(52) U.S. Cl.
CPC .............. *G01T 1/241* (2013.01); *A61B 6/032* (2013.01); *A61B 6/4241* (2013.01)

(58) Field of Classification Search
CPC ... A61B 6/4291; A61B 6/4241; A61B 6/4441; G01T 1/2928; G01T 1/247; G01T 7/005
See application file for complete search history.

(56) References Cited

U.S. PATENT DOCUMENTS

| 9,600,910 B2 | 3/2017 | Wang et al. |
| 9,730,657 B2 | 8/2017 | Wang et al. |
| (Continued) | | |

FOREIGN PATENT DOCUMENTS

| WO | 2014-028930 | 2/2014 |
| WO | 2015164405 A1 | 10/2015 |
| (Continued) | | |

OTHER PUBLICATIONS

Gierada et al., "Gadolinium as a CT contrast agent: assessment in a porcine model," Radiology, Mar. 1999, Abstract, vol. 210, No. 3.
(Continued)

*Primary Examiner* — David P Porta
*Assistant Examiner* — Fani Boosalis
(74) *Attorney, Agent, or Firm* — Murtha Cullina LLP; Anthony P. Gangemi

(57) ABSTRACT

Novel and advantageous methods and systems for performing computed tomography (CT) imaging are disclosed. Electrodes can be connected to appropriate surface sites of a detector element of a CT scanner to capture nearby electron-hole pairs generated by X-rays received on the detector element. This detection can be performed in current-integrating/energy-integrating mode.

19 Claims, 41 Drawing Sheets

(56) References Cited

U.S. PATENT DOCUMENTS

| | | | |
|---|---|---|---|
| 2005/0226361 A1 | 10/2005 | Zhou et al. | |
| 2009/0321643 A1 | 12/2009 | Rutten et al. | |
| 2010/0239064 A1 | 9/2010 | Zhou et al. | |
| 2011/0150187 A1* | 6/2011 | Boudry | H05G 1/46 378/207 |
| 2012/0205549 A1 | 8/2012 | Simon et al. | |
| 2013/0251097 A1 | 9/2013 | Zou | |
| 2014/0126704 A1* | 5/2014 | Zou | H01J 35/025 378/197 |
| 2015/0157286 A1 | 6/2015 | Wang et al. | |
| 2016/0113602 A1 | 4/2016 | Wang et al. | |
| 2016/0135769 A1 | 5/2016 | Wang et al. | |
| 2016/0166852 A1 | 6/2016 | Wang et al. | |
| 2017/0043041 A1 | 2/2017 | Wang et al. | |

FOREIGN PATENT DOCUMENTS

| | | |
|---|---|---|
| WO | 2016106348 A1 | 6/2016 |
| WO | 2016118960 A1 | 7/2016 |
| WO | 2016154136 A1 | 9/2016 |
| WO | 2016197127 A1 | 12/2016 |
| WO | 2017015381 A1 | 1/2017 |
| WO | 2017019782 A1 | 2/2017 |
| WO | 2017048856 A1 | 3/2017 |
| WO | 2017083849 A1 | 5/2017 |
| WO | 2017143247 A1 | 8/2017 |

OTHER PUBLICATIONS

Hwang, "Assessment of Gd-DTPA as contrast agent for CT in rabbit models," American Society of Neurology Annual Meeting, Apr. 2001, Abstract.

Overdick et al., "Status of direct conversion detectors for medical imaging with x-rays," IEEE Transactions on Nuclear Science, Aug. 2009, pp. 1800-1809, vol. 56, No. 4.

Doran et al., "A CCD-based optical CT scanner for high-resolution 3D imaging of radiation dose distributions: equipment specifications, optical simulations and preliminary results," Physics in Medicine and Biology, Nov. 2001, pp. 3191-3213, vol. 46.

Pan et al., "Computed tomography in color: nanoK-enhanced spectral CT molecular imaging," Angewandte Chemie International Edition in English, Dec. 2010, pp. 1-11, Author Manuscript.

Taguchi et al., "Vision 20/20: single photon counting x-ray detectors in medical imaging," Medical Physics, Oct. 2013, pp. 100901-1-100901-19, vol. 40, No. 10.

Bornefalk et al., "Photon-counting spectral computed tomography using silicon strip detectors: a feasibility study," Physics in Medicine and Biology, Mar. 2010, pp. 1999-2022, vol. 55.

Persson et al., "Energy-resolved CT imaging with a photon-counting silicon-strip detector," Physics in Medicine and Biology, Oct. 2014, pp. 6709-6727, vol. 59.

Gruner et al., "Charge-coupled device area x-ray detectors," Review of Scientific Instruments, Aug. 2002, pp. 2815-2842, vol. 73, No. 8.

Alvarez et al., "Energy-selective reconstructions in x-ray computerized tomography," Physics in Medicine and Biology, Sep. 1976, pp. 733-744, vol. 21, No. 5.

Giersch et al., "The influence of energy weighting on x-ray imaging quality," Nuclear Instruments and Methods in Physics Research A, Sep. 2004, pp. 68-74, vol. 531.

Taguchi et al., "An analytical model of the effects of pulse pileup on the energy spectrum recorded by energy resolved photon counting x-ray detectors," Medical Physics, Aug. 2010, pp. 3957-3969, vol. 37, No. 8.

Bertolini et al., "Semiconductor Detectors," Science, Apr. 1970, p. 462, vol. 168.

Chu et al., "Combination of current-integrating/photon-counting detector modules for spectral CT," Physics in Medicine and Biology, Sep. 2013, pp. 7009-7024, vol. 58.

Shikhaliev, "Projection x-ray imaging with photon energy weighting: experimental evaluation with a prototype detector," Physics in Medicine and Biology, Jul. 2009, pp. 4971-4992, vol. 54.

Shikhaliev, "Energy-resolved computed tomography: first experimental results," Physics in Medicine and Biology, Sep. 2008, pp. 5595-5613, vol. 53.

Burke et al., "CCD soft x-ray imaging spectrometer for the ASCA satellite," IEEE Transactions on Nuclear Science, Feb. 1994, pp. 375-385, vol. 41, No. 1.

Lundqvist et al., "Computer simulations and performance measurements on a silicon strip detector for edge-on imaging," 1999 IEEE Nuclear Science Symposium Conference, Oct. 1999, pp. 433-438, Seattle, Washington.

Marcelot et al., "Study of CCD transport on CMOS imaging technology: comparison between SCCD and BCCD, and ramp effect on the CTI," IEEE Transactions on Electron Devices, Mar. 2014, pp. 844-849, vol. 61.

Tompsett, "Surface potential equilibration method of setting charge in charge-coupled devices," IEEE Transactions on Electron Devices, Jun. 1975, pp. 305-309, vol. 22, No. 6.

Hoople et al., "Characteristics of submicrometer gaps in buried-channel CCD structures," IEEE Transactions on Electron Devices, May 1991, pp. 1175-1181, vol. 38, No. 5.

Arfelli et al., "An 'edge-on' silicon strip detector for x-ray imaging," IEEE Transactions on Nuclear Science, Jun. 1997, pp. 874-880, vol. 44, No. 3.

Rigon et al., "A single-photon counting "edge-on" silicon detector for synchrotron radiation mammography," Nuclear Instruments and Methods in Physics Research A, Sep. 2009, pp. S62-S65, vol. 608.

Xu et al., "Image reconstruction for hybrid true-color micro-ct," IEEE Transactions on Biomedical Engineering, Jun. 2012, pp. 1-25, Author Manuscript.

De Man et al., "An iterative maximum-likelihood polychromatic algorithm for ct," IEEE Transactions on Medical Imaging, Oct. 2001, pp. 999-1008, vol. 20, No. 10.

International Search Report and Written Opinion, International Application No. PCT/US2016/014769, PCT/ISA/210, PCT/ISA/237, dated Apr. 25, 2016.

* cited by examiner

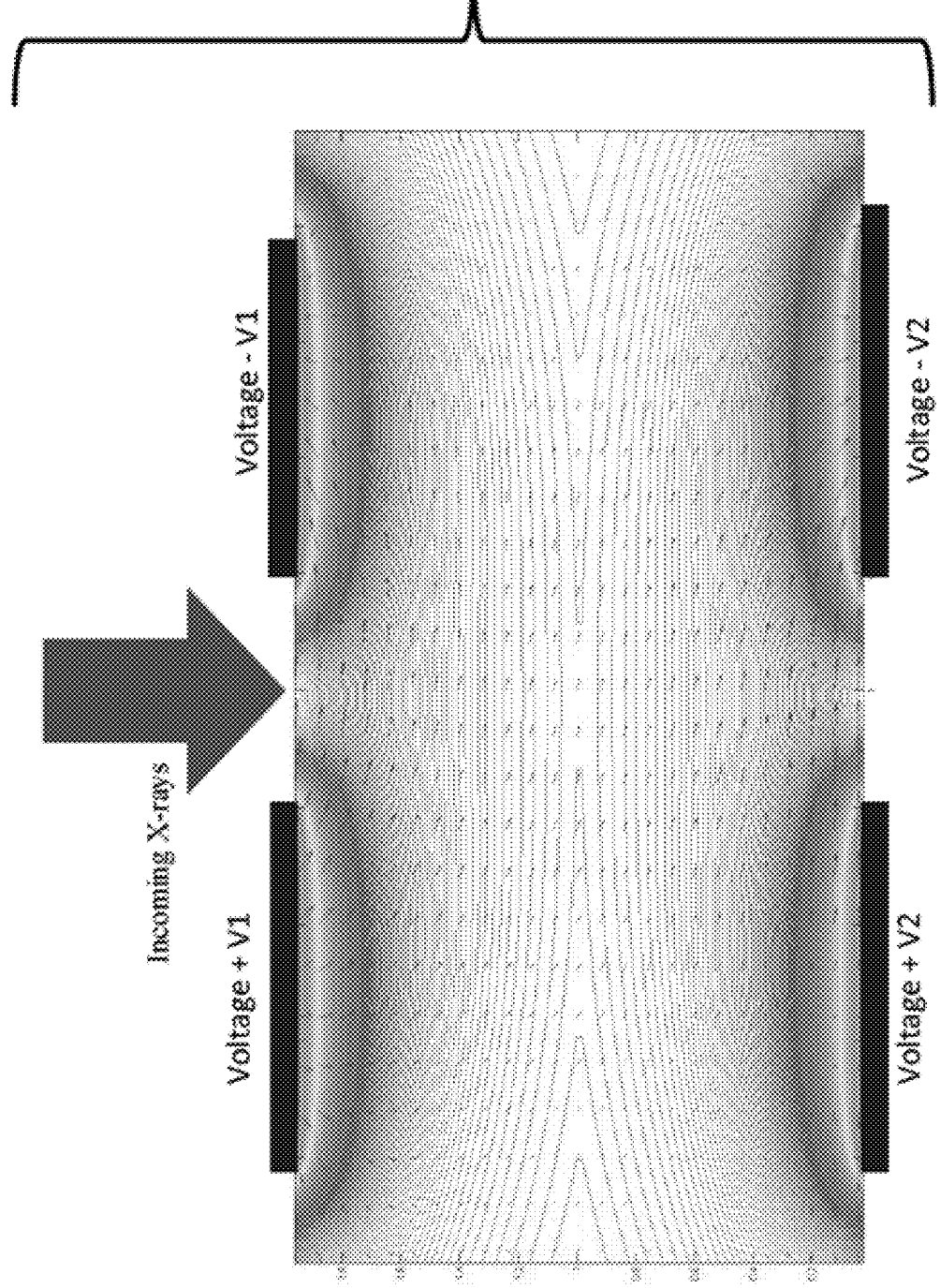

| | Medipix3 | Detector of subject invention |
|---|---|---|
| Dynamic Range | 14 bit | 80 DB / 14 bit |
| Acquisition Time | 1 ms | 40 μs – 1 ms |
| Frame Rate | 500 fps | 1k fps |
| Pixel Size | 110 x 110 μm² <br> 55 x 55 μm² | 650 x 650 μm² |
| Fill Factor | >90% | 85.2% |
| Material & Thickness | 2 mm CdTe <br> 2 mm CZT <br> 300 μm Si <br> 300-900 μm GaAs | 33mm Si |
| Energy Range | 10-50 keV | 10-50 keV |
| Working Mode | Photon Counting | PE & Charge Coupling |

FIG. 14

$$\max_{\mu} \sum_i \left( I_i \cdot \ln\left(\hat{I}_i\right) - \hat{I}_i \right) - \left(\mu - \mu^*\right)^T \cdot \Gamma \cdot \left(\mu - \mu^*\right)$$

Weighting Factor (over $\Gamma$)

Dual-material Decomposition (over $\mu^*$)

FIG. 28

$$I(v,d) = I_0 \int_0^{E_{max}} S(E,v) D(E,d) \exp\left\{-\int \mu(E,r) dr\right\} dE$$

Discretization $$= I_0 \int_0^{E_{max}} S(E,v) D(E,d) \exp\left\{-\int_{-\infty}^{\infty} [\mu_0(E,r) + \Delta\mu(E,r)] dr\right\} dE$$

$$= I_0 \int_0^{E_{max}} S(E,v) D(E,d) \exp\left\{-\int_{-\infty}^{\infty} \mu_0(E,r) dr\right\} \left(1 - \int_{-\infty}^{\infty} \Delta\mu(E,r) dr\right) dE$$

$$A \Delta\mu = b$$

FIG. 29

$$I(v,d) = I_0 \int_0^{E_{max}} S(E,v)D(E,d)exp\left\{-\int_{-\infty}^{\infty} \mu(E,r)dr\right\}dE$$

$$I_m(v,d) - I(v,d) = I_0 \int_0^{E_{max}} S(E,v)D(E,d)B(E)dE \cdot \Delta a$$

$$B(E) = \left[\mu_{water}(E), \mu_{bone}(E), \mu_{Gd}(E)\right]$$

$$\Delta a = \left[\int_{-\infty}^{\infty} \Delta a_1(r)dr, \int_{-\infty}^{\infty} \Delta a_2(r)dr, \int_{-\infty}^{\infty} \Delta a_3(r)dr\right]$$

SPECTRAL X-RAY DETECTORS WITH DYNAMIC ELECTRONIC CONTROL AND COMPUTATIONAL METHODS

CROSS-REFERENCE TO RELATED APPLICATION

The present application is a national stage application of International Patent Application No. PCT/US2016/014769, filed Jan. 25, 2016, which claims the benefit of U.S. Provisional Application Ser. No. 62/107,036, filed Jan. 23, 2015, and U.S. Provisional Application Ser. No. 62/150,887 filed Apr. 22, 2015, both of which are incorporated herein by reference in their entirety, including any figures, tables, and drawings.

BACKGROUND OF INVENTION

Computed Tomography (CT) is a major tool in diagnostic imaging. X-ray detection technology typically uses energy-integrating detectors that add electrical signals, from interactions between an X-ray beam and a material of the detector, over the whole spectrum. Energy-integrating detectors often lose spectral information. Spectral CT (SCT) has advantages over conventional CT by offering detailed spectral information for material decomposition. SCT can also reduce beam-hardening artifacts and radiation dose. However, related art SCT is slower, less stable, and much more expensive than conventional CT.

Conventional CT is based on energy-integrating and/or current-integrating detectors for data acquisition. With photon-counting detectors, SCT can offer additional spectral information for diagnosis, such as discriminating tissues and differentiating calcium and iodine. Related art commercial dual-energy CT technologies include a dual-source CT system from Siemens, a dual-kVp system from GE, and a dual-layer-detector-based system from Philips. These scanners are not for SCT systems because only two material basis functions can be extracted.

BRIEF SUMMARY

The subject invention provides novel and advantageous methods and systems for performing imaging, such as computed tomography (CT) imaging (e.g., spectral CT (SCT) imaging or energy/current integrating CT imaging). Electrical connectors (e.g., electrodes) can be connected to appropriate surface sites of a detector element of a CT scanner to capture nearby electron-hole pairs generated by X-rays received on the detector element. The spectral information of interacting X-ray photons can be related to the site/depth of the interaction between X-rays and the detector material. This process can be accurately modeled, quantified, and/or inverted, according to the penetration/interaction location of the X-rays inside the detector element (e.g., a semiconductor sensor) for direct X-ray detection. This can be based on, for example, the radiative transport equation or its approximation. This detection can be done in the current-/energy-integrating mode.

In an embodiment, an imaging system can include: a CT scanner including an X-ray source; and a detector for receiving X-ray radiation from the X-ray source after it passes through a sample to be imaged. The detector can include a first pair of electrodes and a second pair of electrodes disposed thereon and configured to provide a first voltage and a second voltage, respectively, to the detector. The detector can include a first layer and a second layer, and the first and second pairs of electrodes can be disposed on and apply the first voltage and the second voltage to the first and second layers, respectively.

In another embodiment, a method of imaging can include: providing X-ray radiation to a sample to be imaged; collecting the X-ray radiation with a detector; providing a first voltage to the detector using a first pair of electrodes disposed thereon; and providing a second voltage to the detector using a second pair of electrodes disposed thereon. The detector can include a first layer and a second layer, and the first and second pairs of electrodes can be disposed on and apply the first voltage and the second voltage to the first and second layers, respectively.

BRIEF DESCRIPTION OF THE DRAWINGS

FIG. 1F shows the detector of FIG. 1E but with a close-up view of the electric field lines.

FIG. 2 shows a detector having four layers and with four voltages being applied with electrodes, one voltage applied to each layer. Each current (I1, I2, I3, and I4) is that flowing into the respective circle representing the voltage (V1, V2, V3, and V4). The four layers have thicknesses H1, H2, H3, and H4, respectively. The incoming X-rays first go through the first layer, then the second, and so on.

FIG. 14 shows a table with values of a related art Medipix3 detector and a detector according to an embodiment of the subject invention.

FIG. 28 shows an equation for reconstructing an image using iterative maximum-likelihood and prior image constraint.

FIG. 29 shows equations for summarizing a ray model after linearization.

FIG. 30 shows equations for summarizing a ray model by basis materials.

DETAILED DESCRIPTION

Figure 1A:
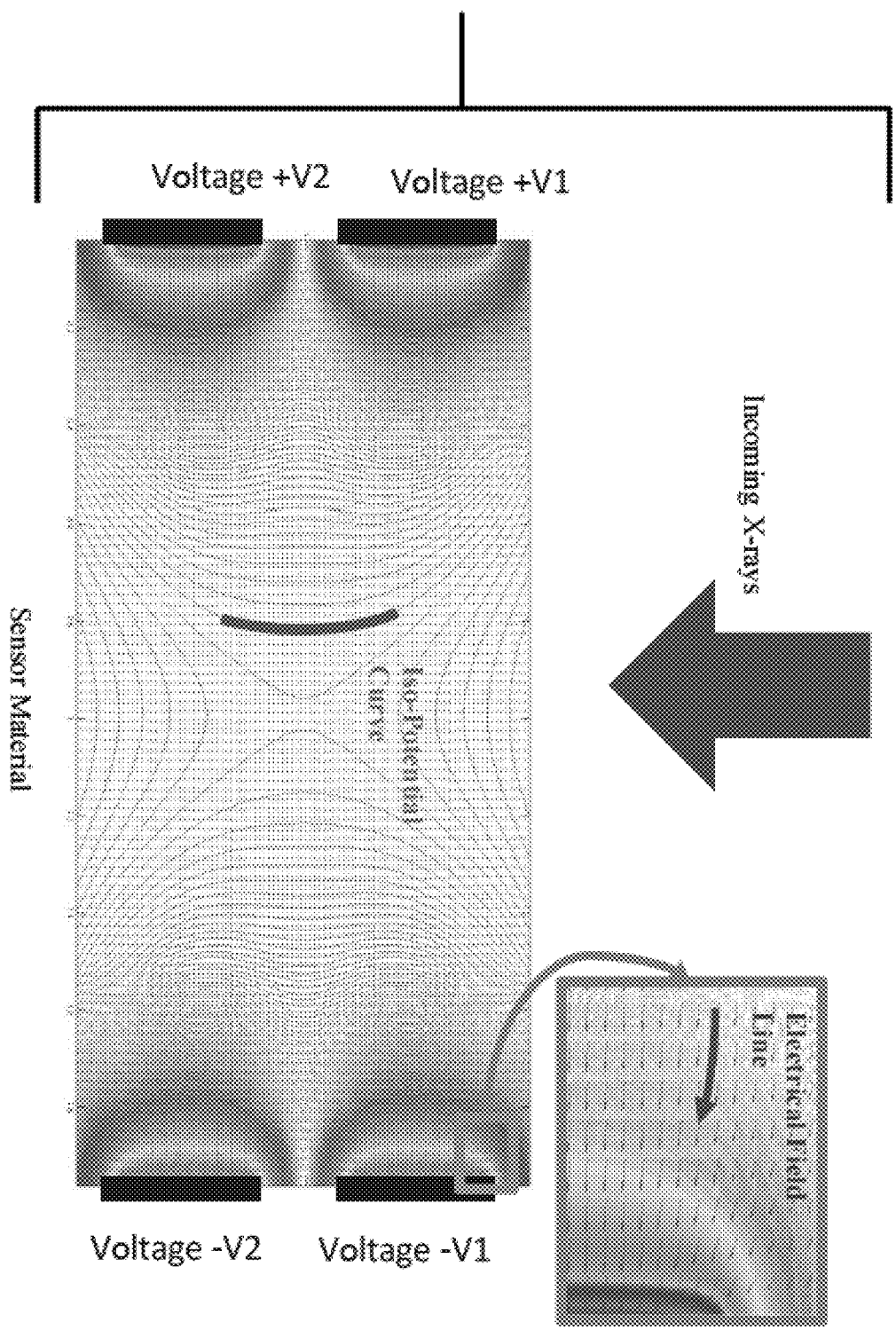
FIG. 1A shows a detector with electrodes disposed parallel to the direction of incoming X-rays, and such that the incoming X-rays are first incident on a side of the detector not having any electrodes disposed thereon. The top electrodes (left and right) as depicted in the figure are an electrode pair, and the bottom two electrodes (left and right) as depicted in the figure are an electrode pair. The electric field lines are based on the voltages of both electrode pairs being equal (V1=V2). The inset shows a zoomed-in view of the electric field lines.

The subject invention provides novel and advantageous methods and systems for performing imaging, such as computed tomography (CT) imaging (e.g., spectral CT (SCT) imaging or energy/current integrating CT imaging). Electrical connectors (e.g., electrodes) can be connected to appropriate surface sites of a detector element of a CT scanner to capture nearby electron-hole pairs generated by X-rays received on the detector element. The spectral information of interacting X-ray photons can be related to the site/depth of the interaction between X-rays and the detector material. This process can be accurately modeled, quantified, and/or inverted, according to the penetration/interaction location of the X-rays inside the detector element (e.g., a semiconductor sensor) for direct X-ray detection. This can be based on, for example, the radiative transport equation or its approximation. This detection can be done in the current-/energy-integrating mode.

Systems and methods of the subject invention can electronically control the collection of spectral information in the current-integration mode on a detector element (e.g., during CT scanning). This can be used with many detection schemes, including dual-layer detectors, SCT detectors, and hybrid detectors.

The voltage(s) applied to the electrodes connected to the detector element can be changed. By changing the voltage(s) applied to the electrodes (or metal plates), the electric field inside the sensor (detector element) can be modified to define various current-conducting layers. For example, two sets of electrodes can be used, and the voltage applied across each set can be the same or different. The voltages can be modified during detection as well. The set of electrodes across which a higher voltage is applied can detect more charges than the same loop driven by a lower voltage. In this way, different spectral ratios between two layers can be obtained for X-ray spectral sensing. This dynamic variation of electrode voltage is very flexible and cost-effective in practice.

The detector configuration having electrodes connected thereto for voltage modification/modulation is quite different and advantageous compared to related art scanners, such as the dual-layer detector design (e.g., that used in the Philips CT scanner). In embodiments of the subject invention, direct X-ray detection can be used such that data acquisition can be dynamically modulated by voltage into higher and lower bins in a desirable ratio. Any ratio can be used, such as 2:1 (higher energy bin:lower energy bin), 3:1, 4:1, 1:2, 1:3, 1:4, 5:1, 1:5, 1.5:1, 1:1.5. These ratios are for exemplary purposes and should not be construed as limiting. Embodiments of the subject invention can be used in a detector having any number of layers, such as two layers (dual layer), three layers (triple layer), four layers (quadruple layer), five layers, or more. A first layer can be made sensitive to low-energy photons while letting most of the high-energy photons penetrate through to subsequent layers. In certain embodiments, the multiple layers can all be the same material (e.g., the material of the detector element sensor) and can be defined by electrode sets such that a first electrode set defines a first layer, a second electrode set defines a second layer, etc.

The detector can include a sensor material, including at least one of cadmium zinc telluride (CZT), silicon (e.g., $p^-$, $p^+$, $n^-$, or $n^+$ silicon), and cadmium telluride (CdTe), though embodiments are not limited thereto. In an embodiment, the detector sensor material is silicon. In a further embodiment, the detector sensor material is $p^-$ silicon In another embodiment, the detector sensor material is CZT.

In an embodiment, a dual-layer detector can break the X-ray spectrum into low and high energies at different proportions during detection. For example, the low and high energies can be broken into proportions of 10%/90%, 20%/80%, 70%/30%, 60%/40%, 50%/50%, 40%/60%, 30%, 70%, 20%/80%, and 10%/90%. These proportions are for exemplary purposes and should not be construed as limiting. In a further embodiment, these detector variants can be distributed in a natural sequence and repeated until a full detector ring is covered in third generation geometry. The breaking of the X-ray spectrum can be performed by changing the applied voltages and/or by using software to read the detected radiation. This breaking of the X-ray spectrum can be applied to multi-layer detectors with more than two layers as well.

Related-art dual-layer detectors use fixed layers and cannot be adapted well for many applications, and related art photon-counting (SCT) detectors are slow and expensive. Embodiments of the subject invention advantageously fill in a gap between these two types of detectors, making up for disadvantages of both. Systems and methods of the subject invention can provide significantly improved performance compared to related art dual-energy CT scanners (approaching SCT performance) while avoiding the high cost and rate limitations of photon-counting (SCT) detectors. Systems and methods of the subject invention therefore have many uses in medical imaging.

Figure 6:
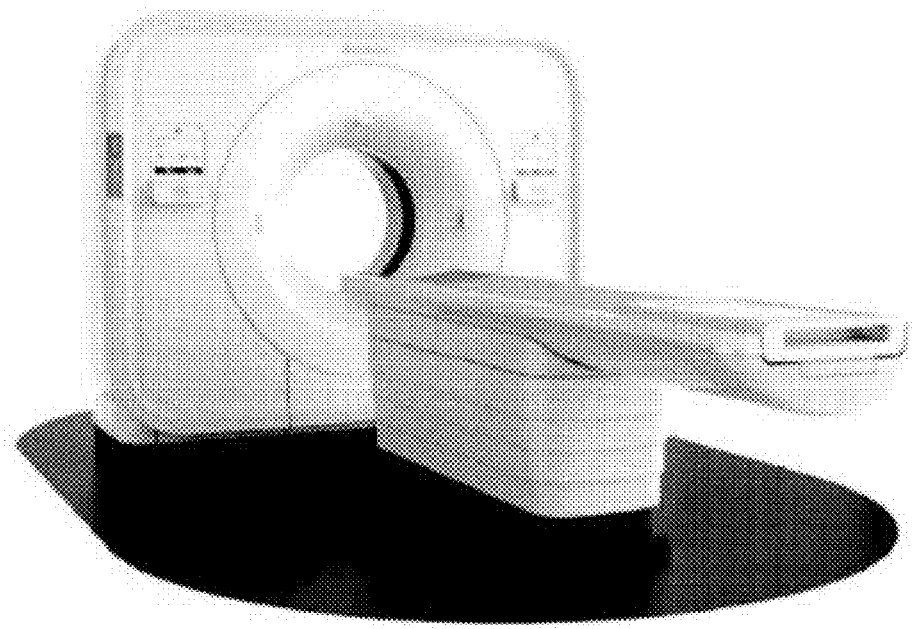
FIG. 6 shows a schematic view of an X-ray CT scanner.
Figure 7:
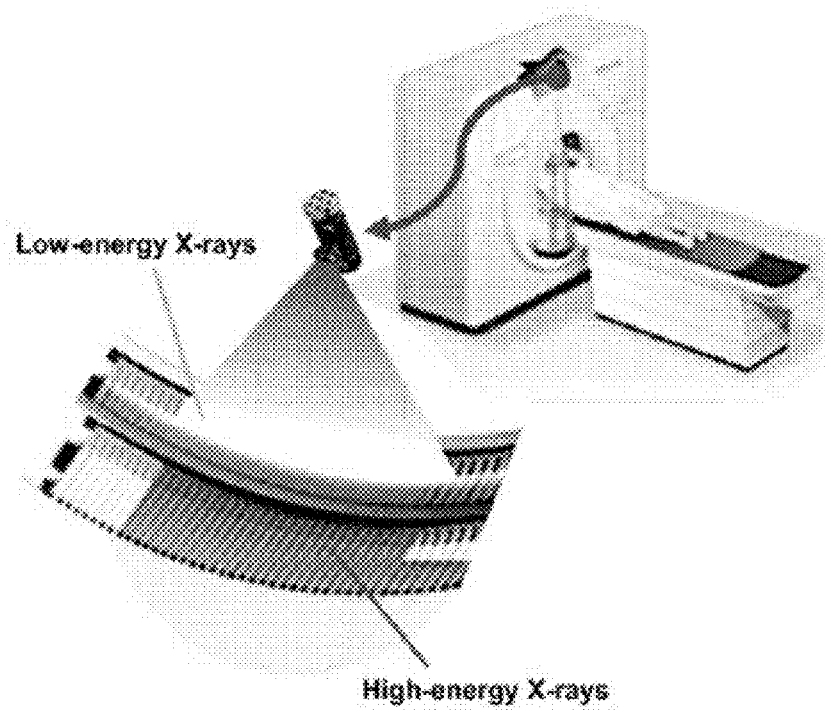
FIG. 7 shows a view of a scanner with an enlarged view of a dual-layer detector, where one layer detects low-energy X-rays and the other layer detects high-energy X-rays.
Figure 8:
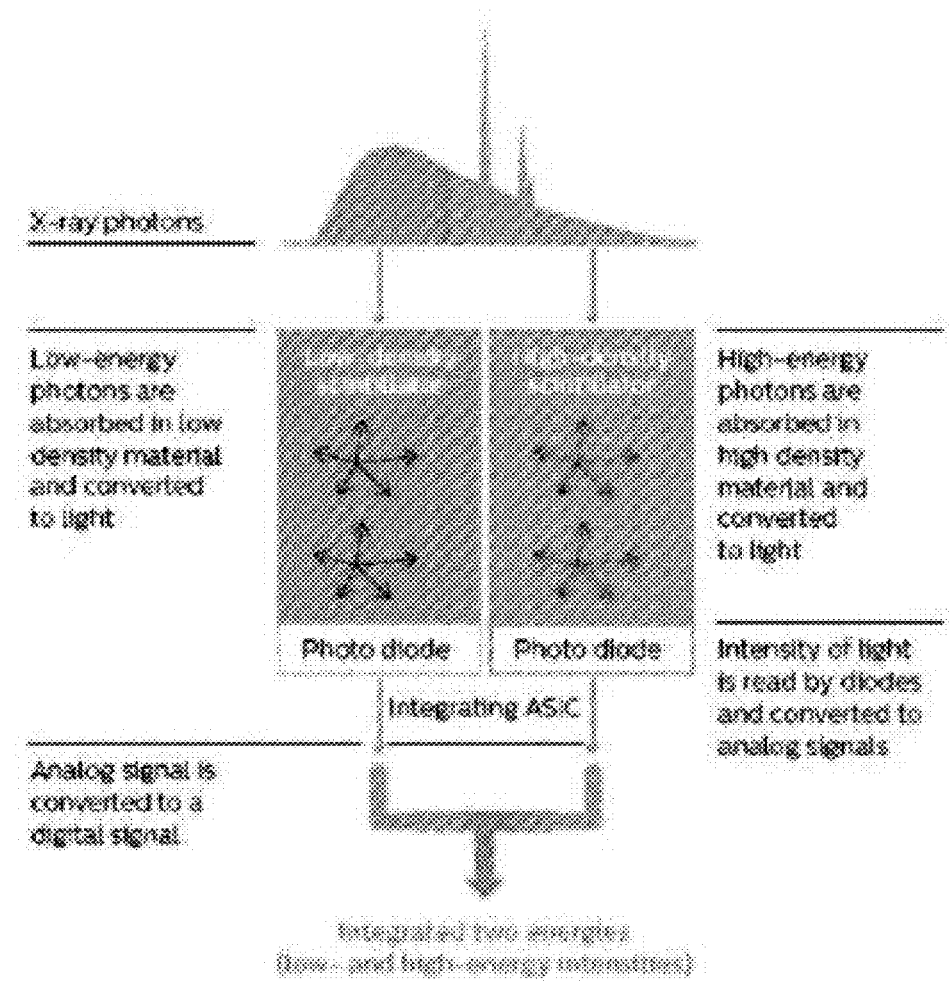
FIG. 8 shows a schematic view demonstrating reading of X-ray photons from a detector.
Figure 9:
FIG. 9 shows an image obtained from a dual-energy CT scanner.
Figure 10:
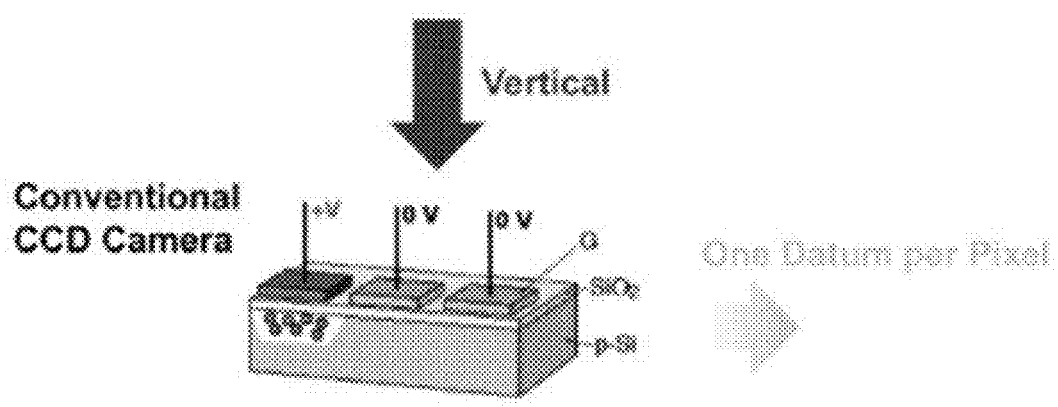
FIG. 10 shows a schematic view of a conventional charge-coupled device (CCD) camera.
Figure 11:
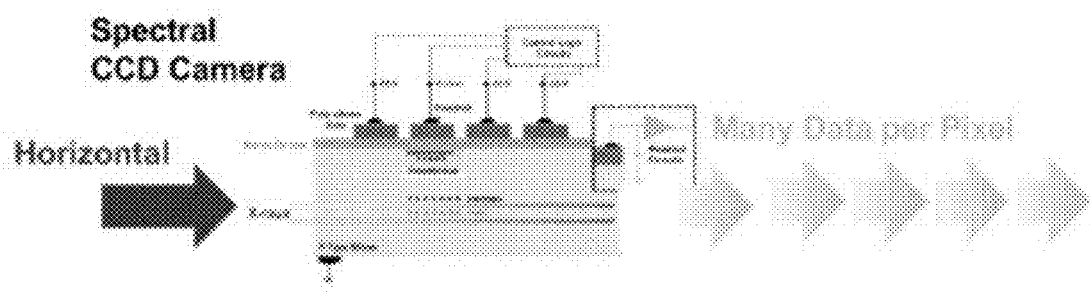
FIG. 11 shows a schematic view of a spectral CCD camera that can be used according to an embodiment of the subject invention.
Figure 12:
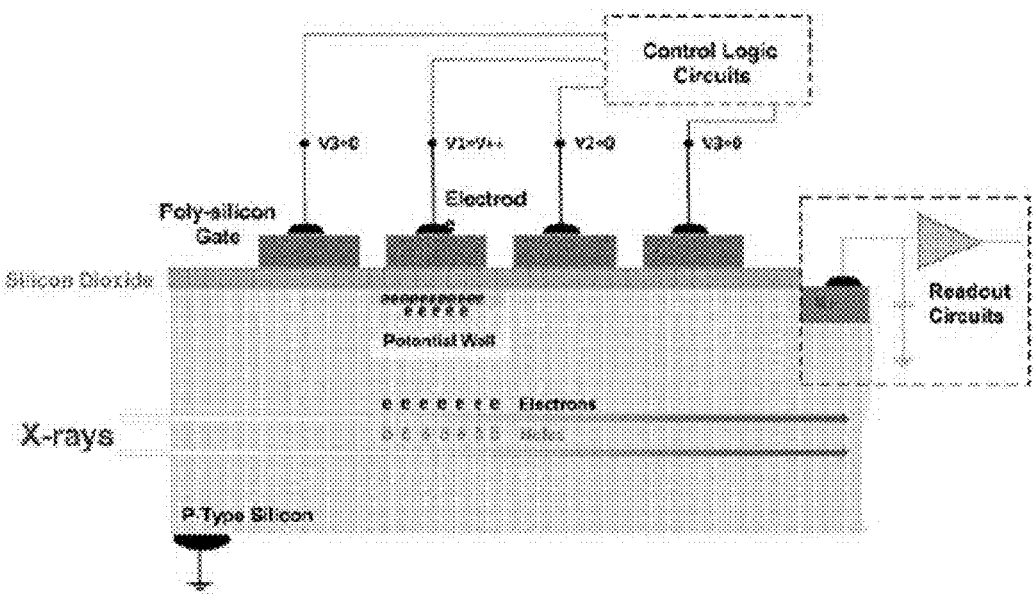
FIG. 12 shows a schematic view of a spectral CCD camera that can be used according to an embodiment of the subject invention, demonstrating charge generation and collection.
Figure 13:
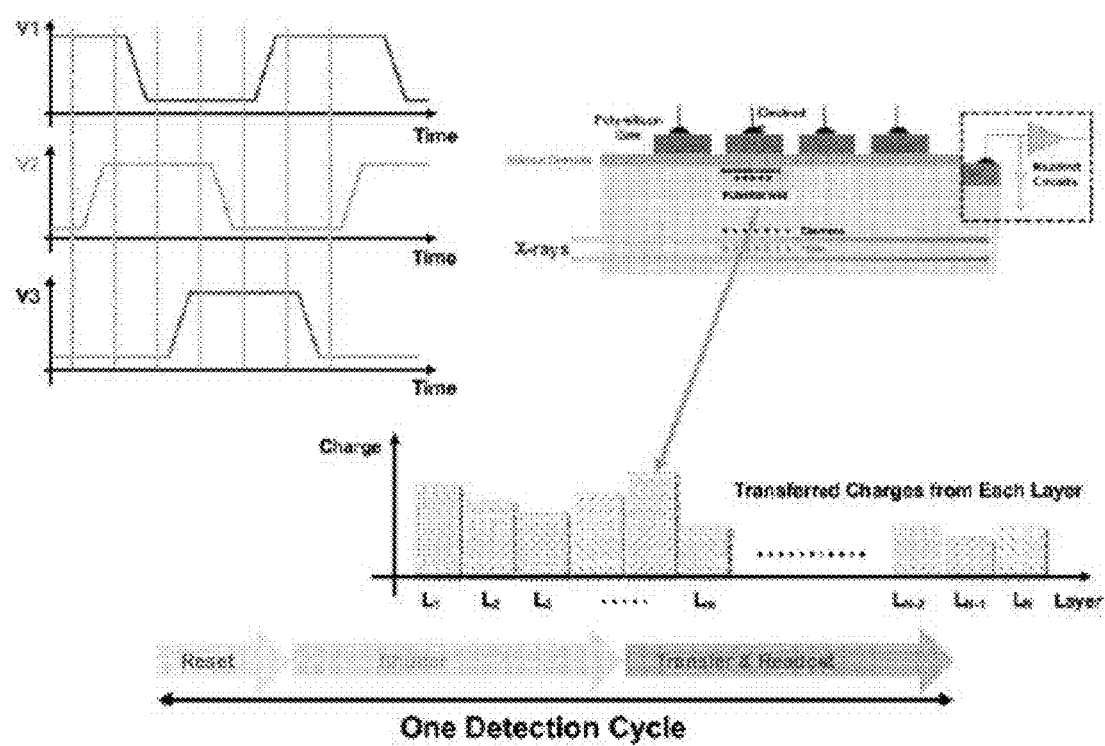
FIG. 13 shows a schematic view of a spectral CCD camera that can be used according to an embodiment of the subject invention, demonstrating energy resolving.
Figure 15:
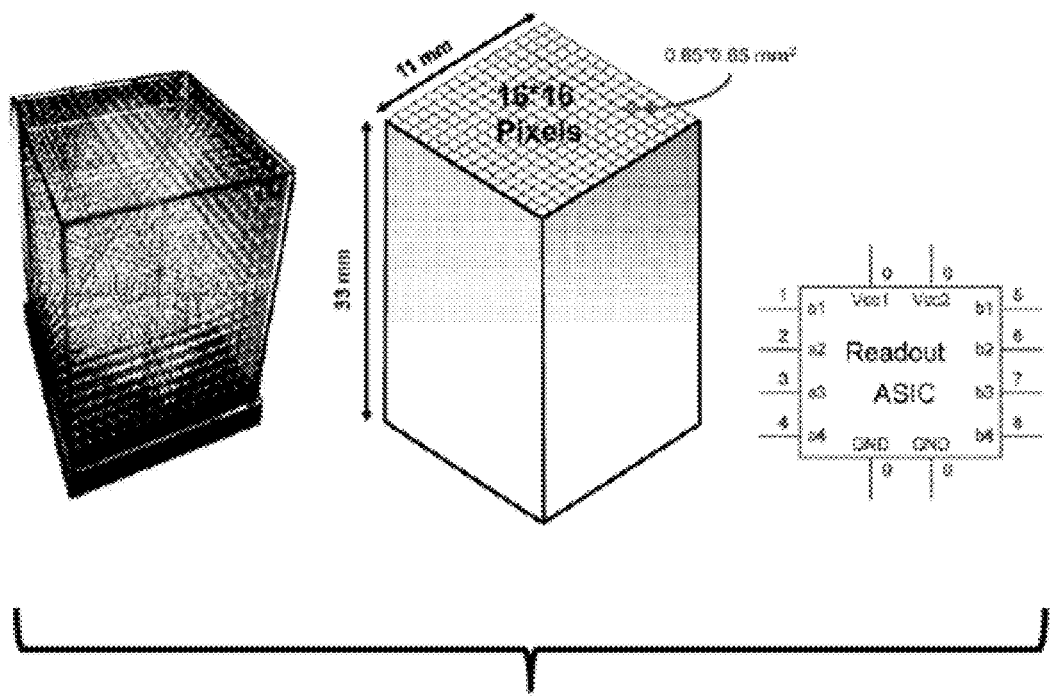
FIG. 15 shows a schematic view of a pixelated detector demonstrating reading of X-ray photons from a detector.
Figure 16A:
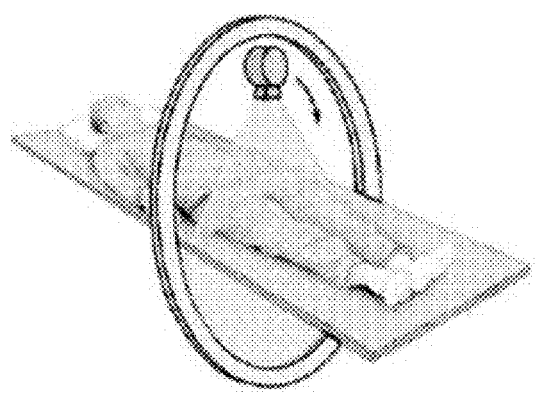
FIG. 16A shows a schematic view of direct detection of X-ray CT for fourth generation geometry. The detector is shown around the human subject being imaged.
Figure 16B:
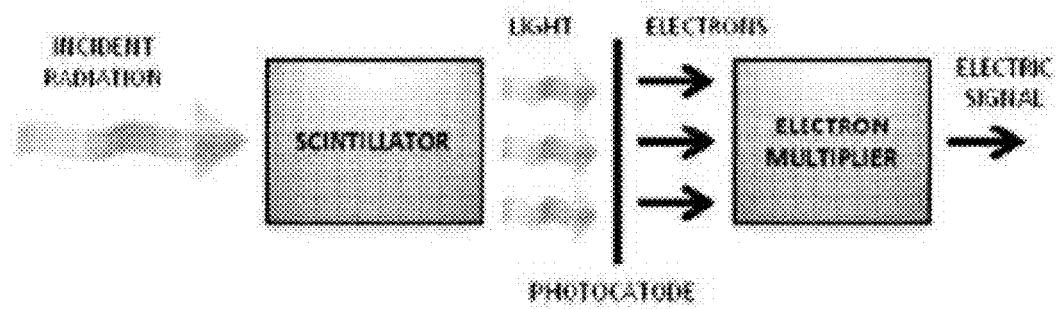
FIG. 16B shows a flow diagram demonstrating direct detection of X-ray CT for fourth generation geometry.
Figure 17:
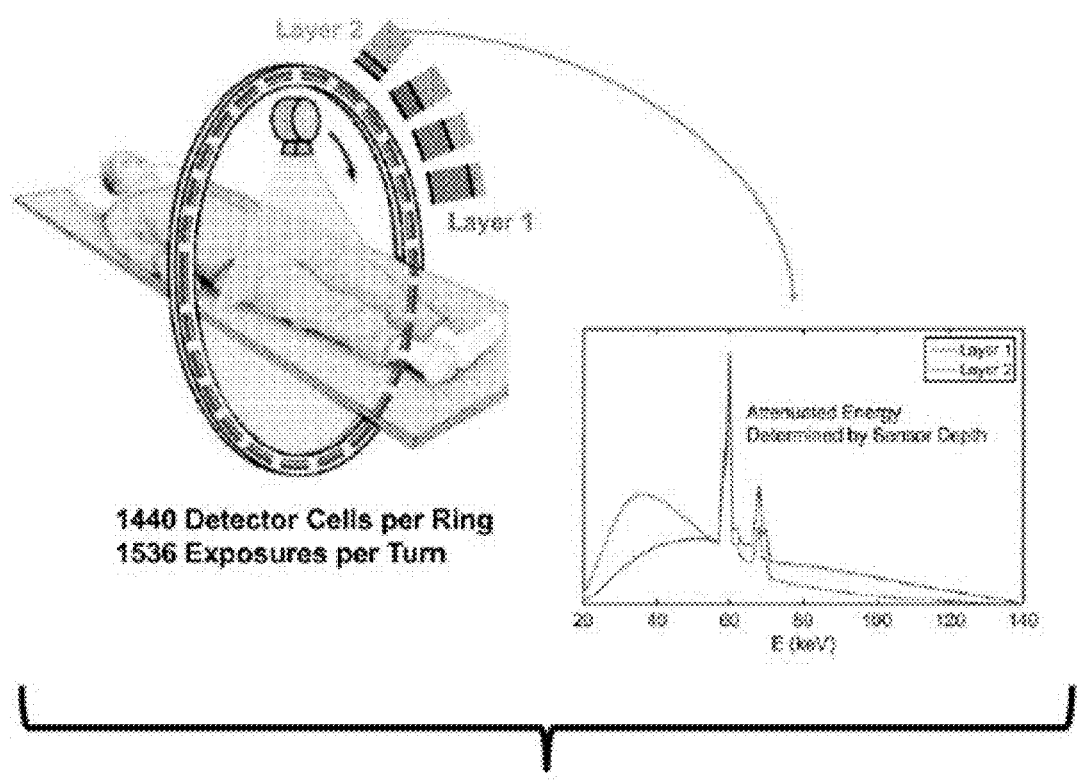
FIG. 17 shows a two-layer detector used as part of fourth generation geometry. The inset shows a detection plot for the first and second layers. The y-axis of the detection plot is photons/second. The first layer is closer to the X-ray source during detection, and has the higher value at lower energy in the plot.

FIGS. 6 and 7 show schematic views of X-ray CT scanners, with FIG. 7 including an enlarged view of a dual-layer detector, where one layer detects low-energy X-rays and the other layer detects high-energy X-rays. FIG. 8 demonstrates reading of X-ray photons from a detector, and FIG. 9 shows an image obtained from a dual-energy CT scanner. FIG. 15 shows a schematic view of a pixelated detector demonstrating reading of X-ray photons from a detector, and FIG. 16A shows a schematic view of direct detection of X-ray CT for fourth generation geometry. The detector is shown around the human subject being imaged. FIG. 16B shows a flow diagram demonstrating direct detection of X-ray CT for fourth generation geometry, and FIG. 17 shows a two-layer detector used as part of fourth generation geometry. The inset of FIG. 17 shows a detection plot for the first and second layers. The y-axis of the detection plot is photons/second. The first layer is closer to the X-ray source during detection, and has the higher value at lower energy in the plot.

Systems and methods of the subject invention can electronically control multi-layer detectors (e.g., dual layer detectors) to acquire X-ray photons in two (or more) energy bins, which can be effectively changed under voltage control. FIGS. 1A-1H show detectors according to embodiments of the subject invention. Referring to FIGS. 1A-1H, a detector can include at least one electrode set for applying a voltage. The electrodes can be disposed in various configurations. In many embodiments, at least one set of electrodes is provided for each layer of the detector. The set of electrodes can define the layers of the detector. In a further embodiment, at least two sets of electrodes can be provided for each layer of the detector.

Figure 1B:
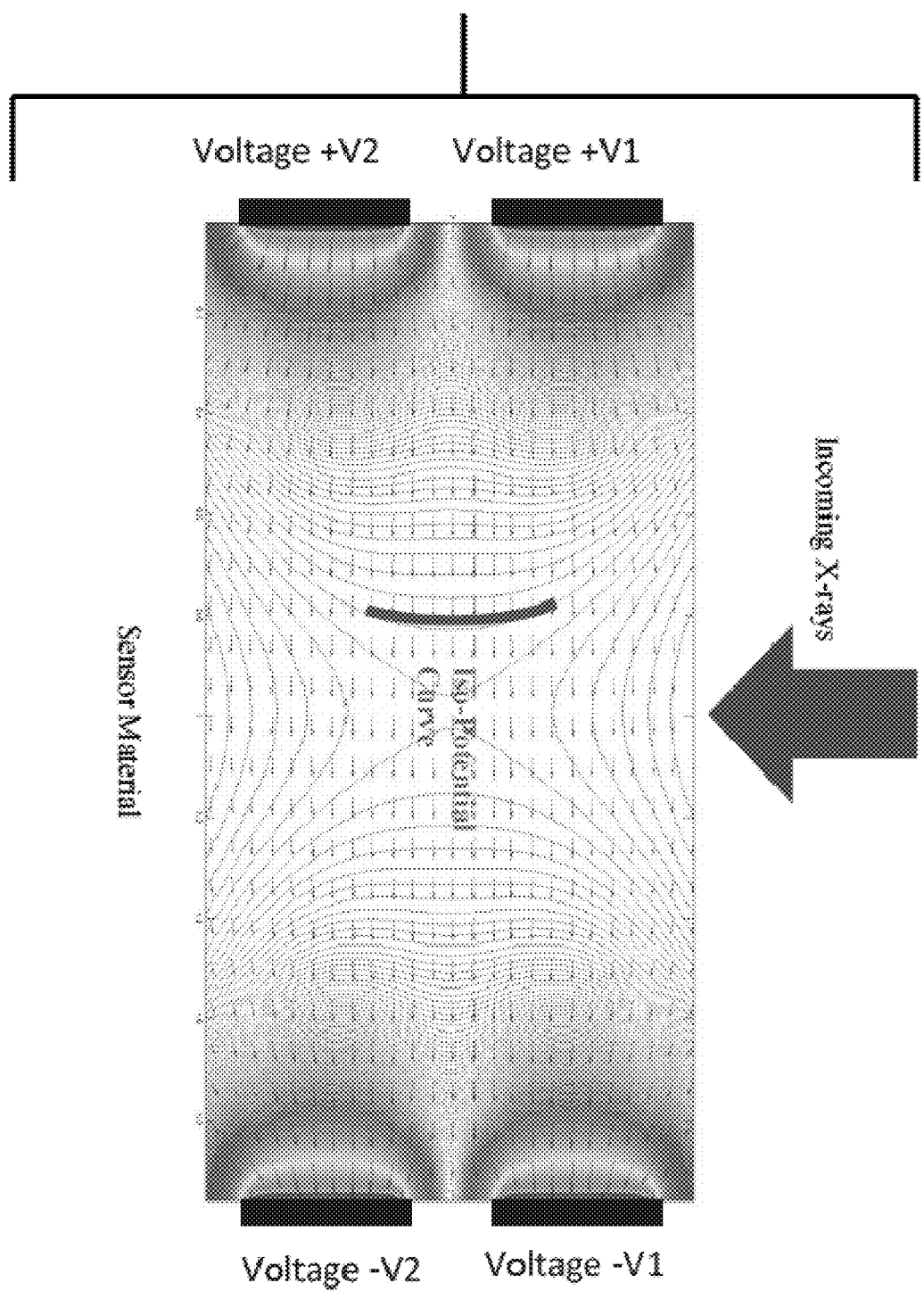
FIG. 1B shows the detector of FIG. 1A but with a close-up view of the electric field lines.

FIG. 1A shows a detector including electrodes disposed parallel to the direction of incoming X-rays, in positions such that the incoming X-rays are first incident on a side of the detector not having any electrodes disposed thereon. The top electrodes (left and right) as depicted in FIG. 1A are an electrode pair, and the bottom two electrodes (left and right) as depicted in FIG. 1A are an electrode pair. The electric field lines are based on the voltages of both electrode pairs being equal (V1=V2). The inset shows a zoomed-in view of the electric field lines. FIG. 1B shows the detector of FIG. 1A but with a close-up view of the electric field lines.

Figure 1C:
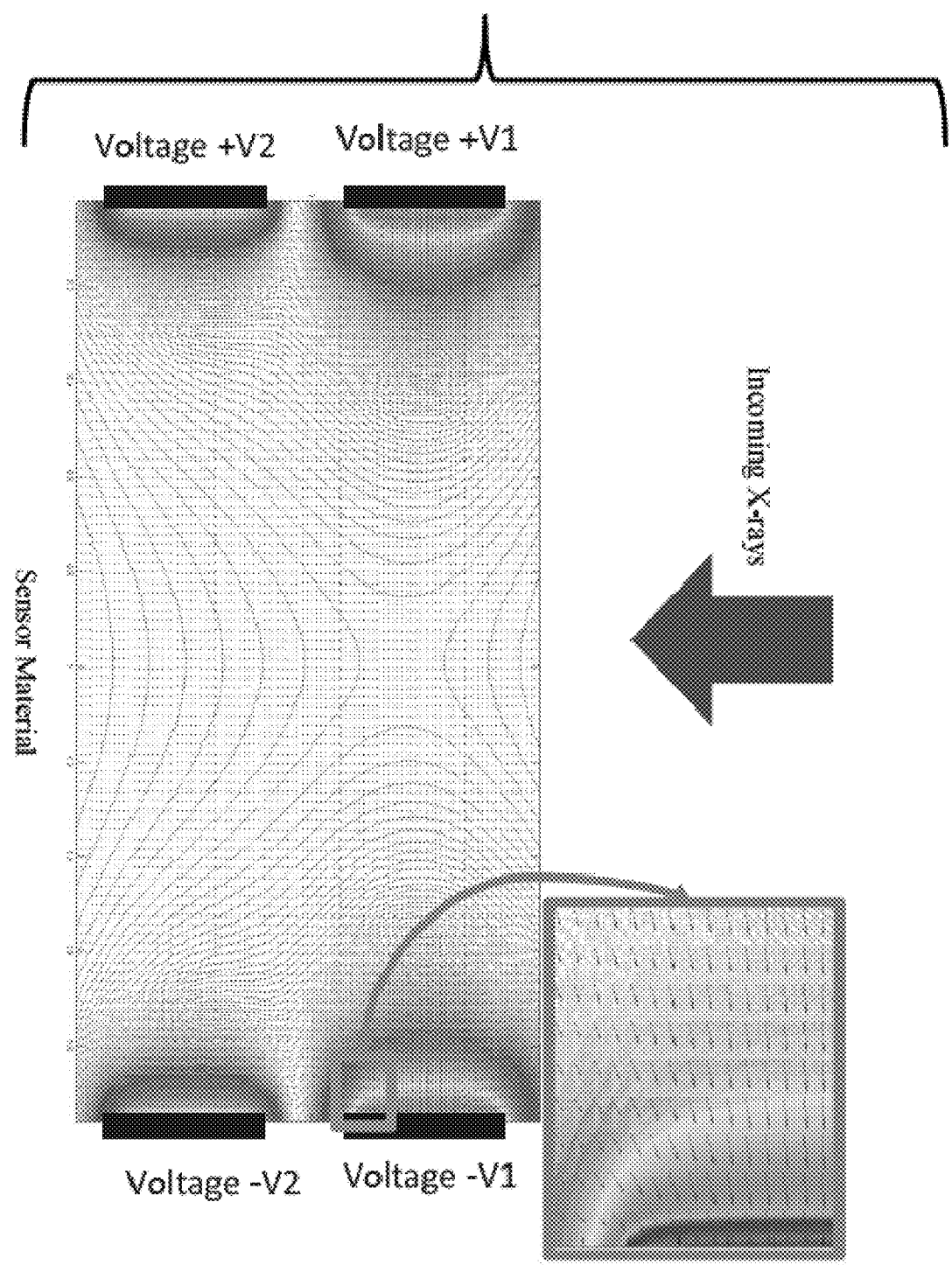
FIG. 1C shows a detector with electrodes disposed parallel to the direction of incoming X-rays, and such that the incoming X-rays are first incident on a side of the detector not having any electrodes disposed thereon. The top electrodes (left and right) as depicted in the figure are an electrode pair, and the bottom two electrodes (left and right) as depicted in the figure are an electrode pair. The electric field lines are based on the voltage of the bottom pair being greater than that of the top pair (V2>V1). The inset shows a zoomed-in view of the electric field lines.
Figure 1D:
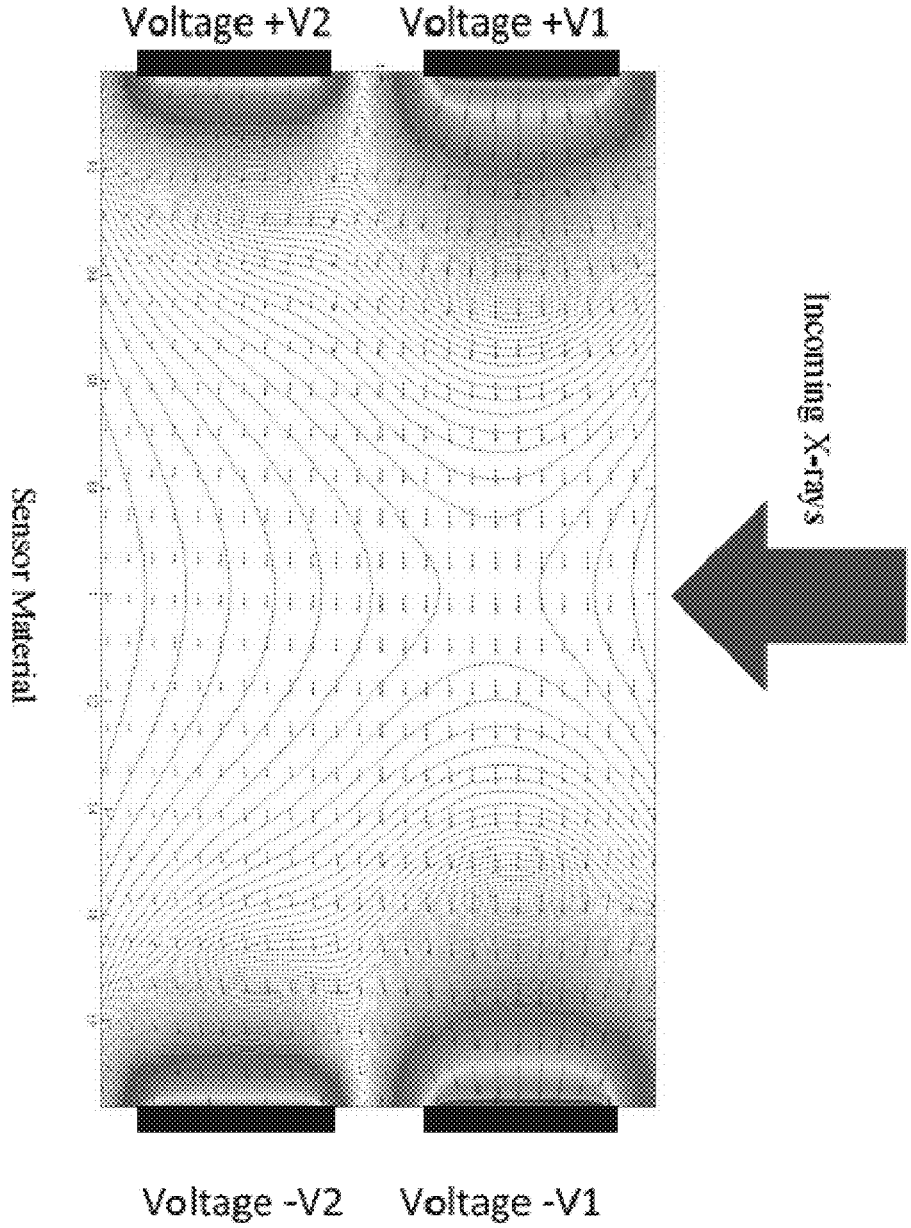
FIG. 1D shows the detector of FIG. 1C but with a close-up view of the electric field lines.

FIG. 1C shows a detector with electrodes disposed parallel to the direction of incoming X-rays, in positions such that the incoming X-rays are first incident on a side of the detector not having any electrodes disposed thereon. The top electrodes (left and right) as depicted in FIG. 1C are an electrode pair, and the bottom two electrodes (left and right) as depicted in FIG. 1C are an electrode pair. The electric field lines are based on the voltage of the bottom pair being greater than that of the top pair (V2>V1). The inset shows a zoomed-in view of the electric field lines. FIG. 1D shows the detector of FIG. 1C but with a close-up view of the electric field lines.

Figure 1E:
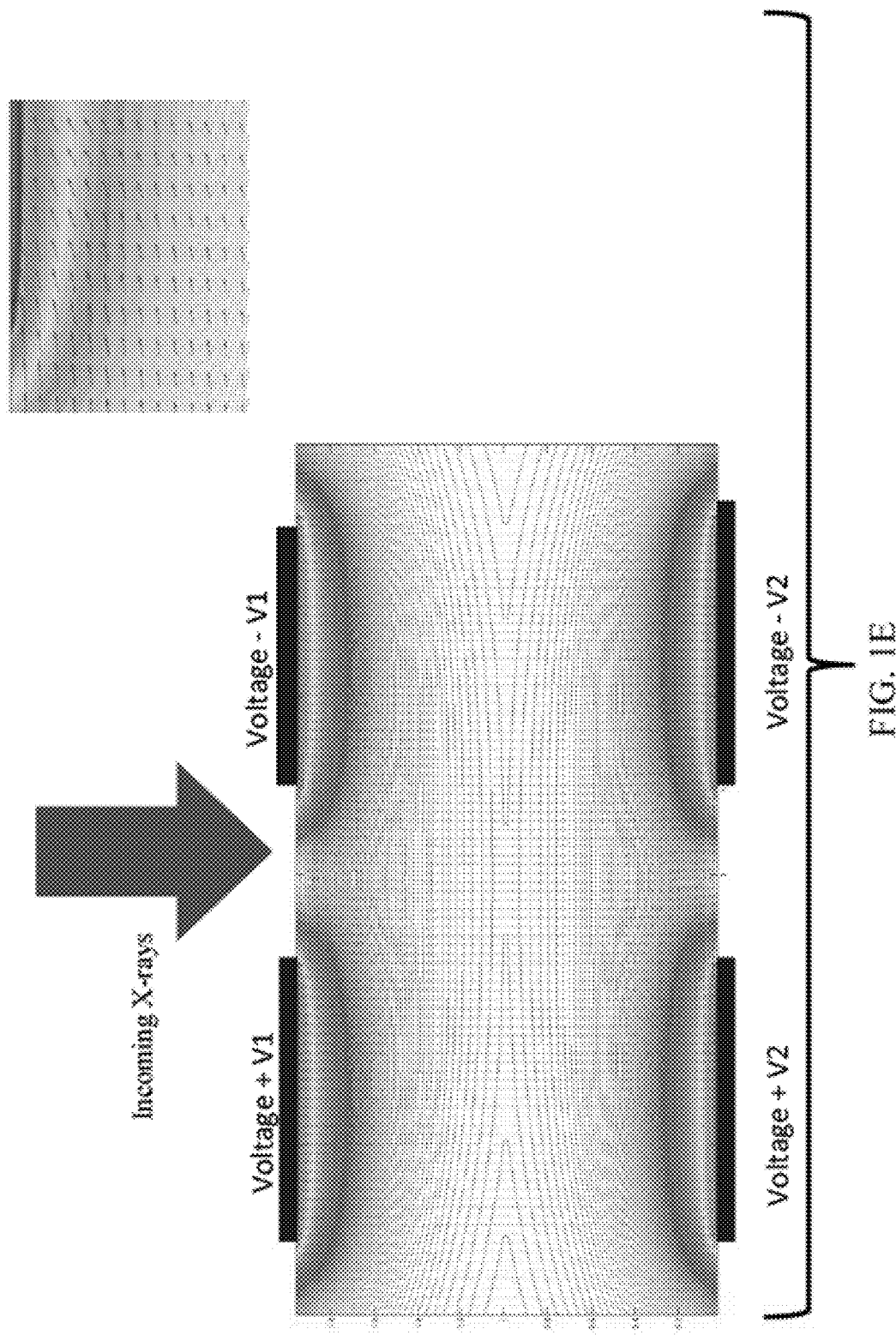
FIG. 1E shows a detector with electrodes disposed perpendicular to the direction of incoming X-rays, and such that the incoming X-rays are first incident on a side of the detector having electrodes disposed thereon. The top electrodes (left and right) as depicted in the figure are an electrode pair, and the bottom two electrodes (left and right) as depicted in the figure are an electrode pair. The electric field lines are based on the voltages of both electrode pairs being equal (V1=V2). The inset shows a zoomed-in view of the electric field lines.

FIG. 1E shows a detector with electrodes disposed perpendicular to the direction of incoming X-rays, in positions such that the incoming X-rays are first incident on a side of the detector having electrodes disposed thereon. The top electrodes (left and right) as depicted in FIG. 1E are an electrode pair, and the bottom two electrodes (left and right) as depicted in FIG. 1E are an electrode pair. The electric field lines are based on the voltages of both electrode pairs being equal (V1=V2). The inset shows a zoomed-in view of the electric field lines. FIG. 1F shows the detector of FIG. 1E but with a close-up view of the electric field lines.

Figure 1G:
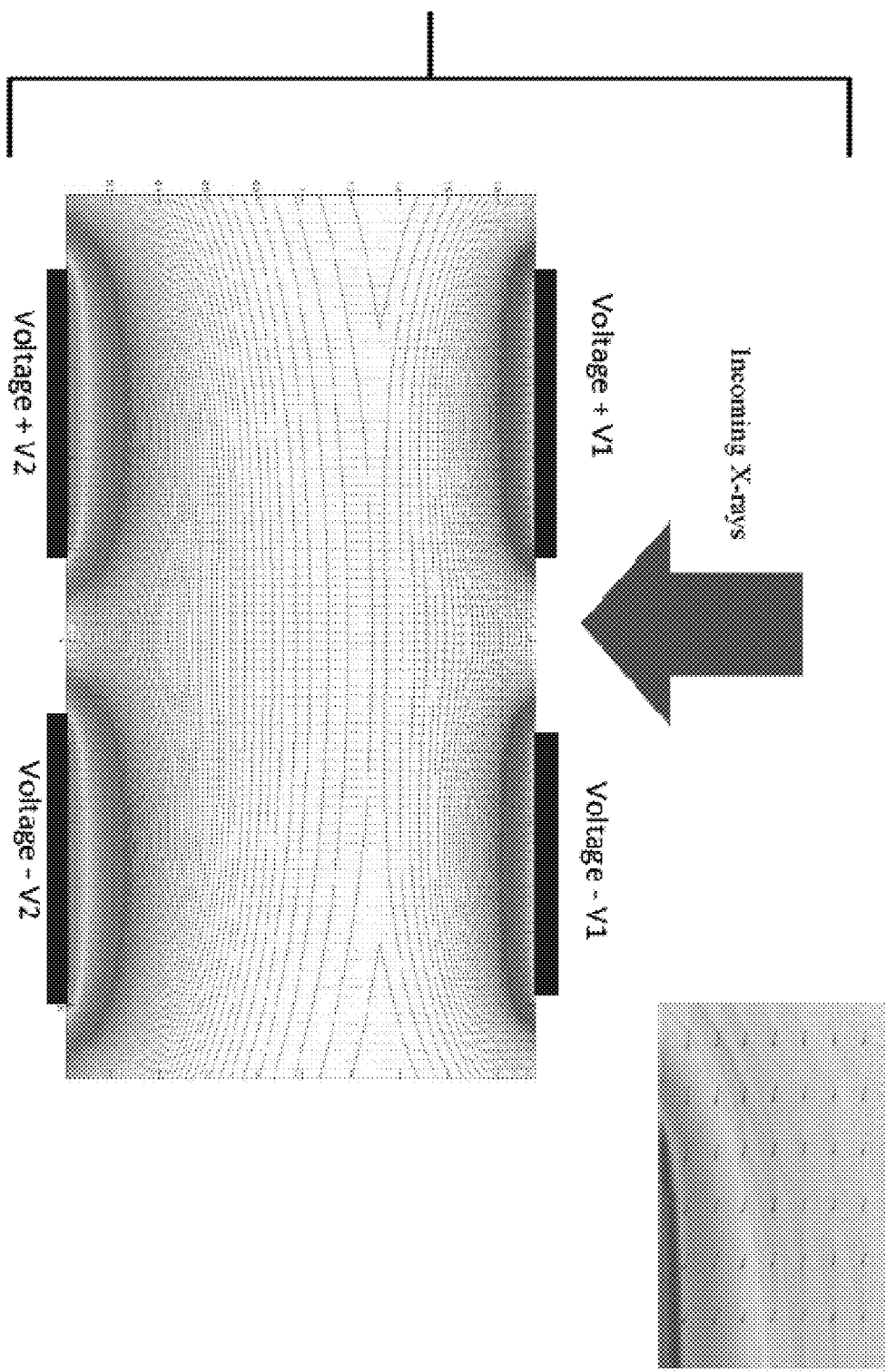
FIG. 1G shows a detector with electrodes disposed perpendicular to the direction of incoming X-rays, and such that the incoming X-rays are first incident on a side of the detector having electrodes disposed thereon. The top electrodes (left and right) as depicted in the figure are an electrode pair, and the bottom two electrodes (left and right) as depicted in the figure are an electrode pair. The electric field lines are based on the voltage of the bottom pair being greater than that of the top pair (V2>V1). The inset shows a zoomed-in view of the electric field lines.
Figure 1H:
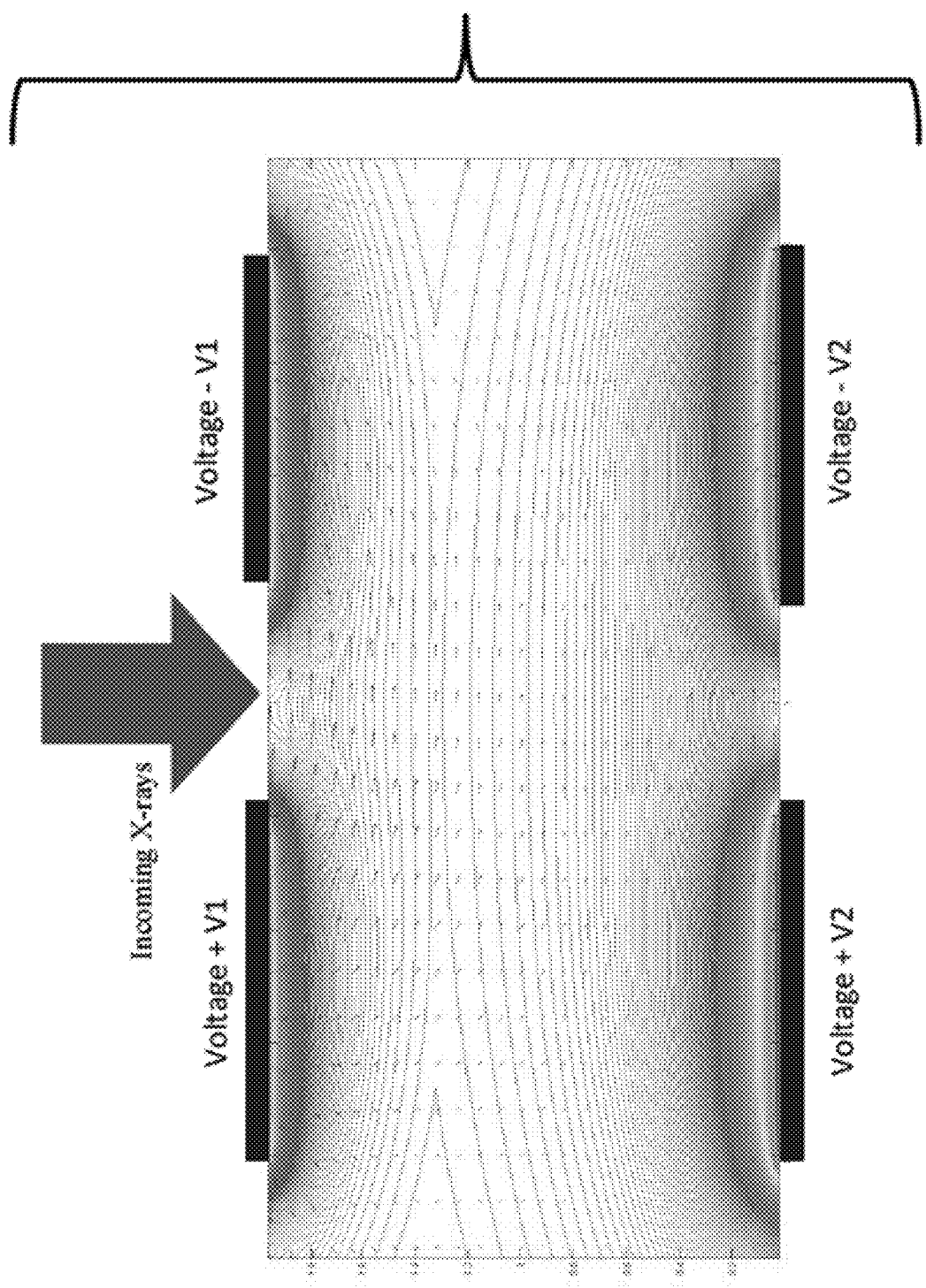
FIG. 1H shows the detector of FIG. 1G but with a close-up view of the electric field lines.

FIG. 1G shows a detector with electrodes disposed perpendicular to the direction of incoming X-rays, in positions such that the incoming X-rays are first incident on a side of the detector having electrodes disposed thereon. The top electrodes (left and right) as depicted in FIG. 1G are an electrode pair, and the bottom two electrodes (left and right) as depicted in FIG. 1G are an electrode pair. The electric field lines are based on the voltage of the bottom pair being greater than that of the top pair (V2>V1). The inset shows a zoomed-in view of the electric field lines. FIG. 1H shows the detector of FIG. 1G but with a close-up view of the electric field lines.

Figure 2:
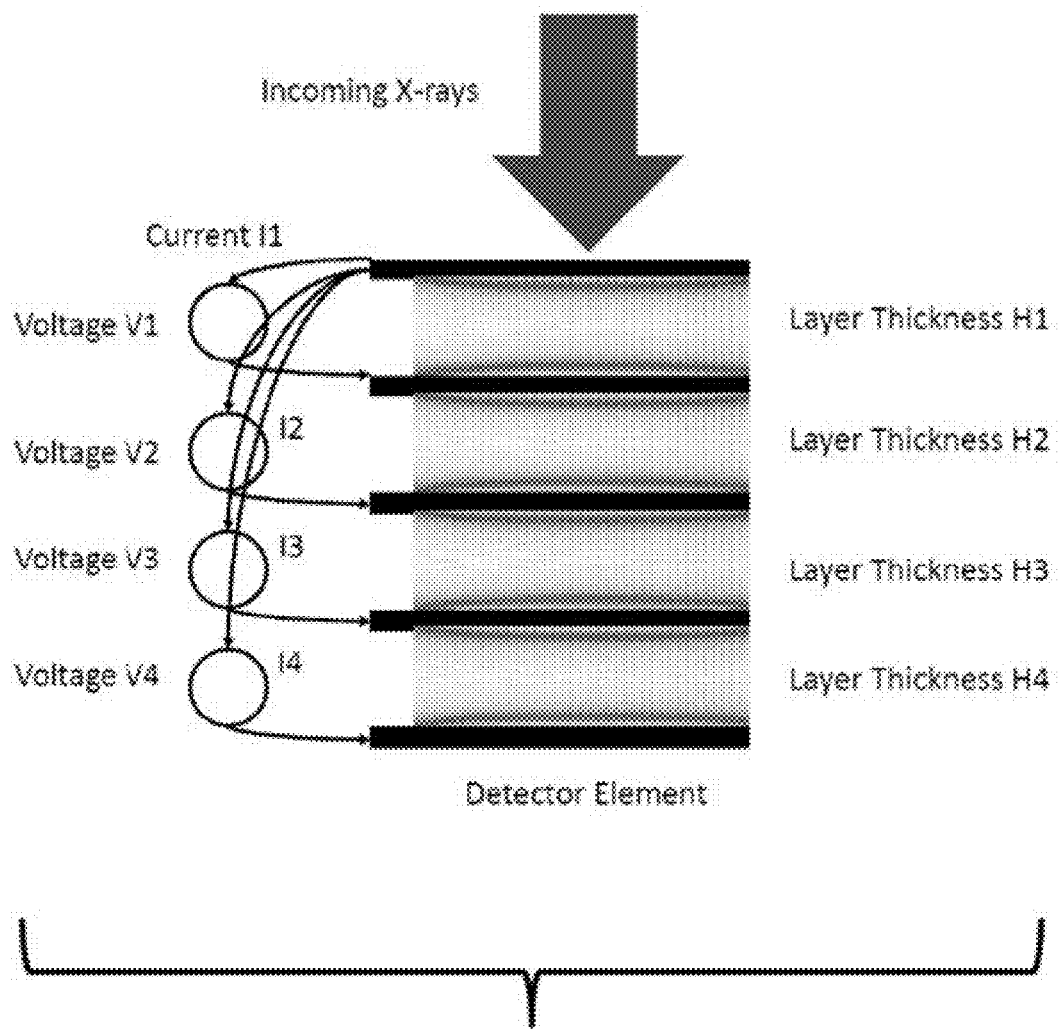

FIG. 2 shows a detector having four layers and with four voltages being applied with electrodes, one voltage applied to each layer. Each current (I1, I2, I3, and I4) is that flowing into the respective circle representing the voltage (V1, V2, V3, and V4). The four layers have thicknesses H1, H2, H3, and H4, respectively. The incoming X-rays first go through the first layer (having thickness H1), then the second, and so on. The thicknesses (H1, H2, H3, and H4) can be all the same, all different, or some can be the same as at least one other while others are different from at least one other.

Referring to FIG. 2, depending on the relative strengths of paired driving voltages V1, V2, V3, and V4, the loop currents I1, I2, I3, and I4 can be solved using Kirchhoff's voltage law (KVL) or Kirchhoff's current law (KCL), both of which are well-known within the art. These data can be used to compute interaction rates in each of the four layers of thicknesses H1, H2, H3, and H4. These interaction rates can be converted to data inside four energy windows in the current-integrating mode of the detector. This allows electrodes to be placed within the detector material and can be extended to other configurations as well.

In embodiments of the subject invention, electrical connectors (e.g., electrode sets or electrode pairs) can be connected to appropriate surface sites of the detector to capture nearby electron-hole pairs. The energy information can be related to the site/depth of the interaction between X-rays and the detector material. In certain embodiments, this process can be modeled, quantified, and/or inverted, according to the penetration depth of the X-ray(s) into the detector material (e.g., semiconductor sensor material) for direct X-ray detection. This can be based, for example, on the radiative transport equation or its approximation.

The voltages applied to the metallic plates/electrodes can be changed, thereby modifying the electric field to define various current-conducting layers. For example, the electrodes across which a higher voltage is applied can detect more charges than those across which a lower is applied (i.e., a lower voltage loop). This can lead to the obtaining of different spectral ratios (as disclosed herein) for X-ray spectral sensing. This dynamic variation of electrode voltage is very flexible and cost-effective in practice.

X-ray detection technology includes energy-integration detection and photon-counting detection. Related art X-ray scanners typically use energy-integrating detectors where electrical signals, from interactions between an X-ray beam and materials, are added up over the whole spectrum. In contrast, photon-counting detectors count photons with energy bins. Photon-counting detectors have advantages relative to energy-integrating detectors are also slower and more expensive. The systems and methods described herein can be considered different from energy-integrating detectors and photon-counting detectors by having the ability to record spectral CT data with voltage-controlled layers. These systems and methods have many practical applications, including but not limited to preclinical imaging, clinical imaging, security screening, and industrial evaluation.

This application shares some aspects with International Patent Application No. PCT/US2015/067441, filed Dec. 22, 2015, and U.S. Provisional Application Ser. No. 62/095,235, filed Dec. 22, 2014, both of which are hereby incorporated herein by reference in their entirety, including any figures, tables, and drawings (see also FIGS. 10-13 of the subject application).

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

The subject invention includes, but is not limited to, the following exemplified embodiments.

Embodiment 1

An imaging system, comprising:
a computed tomography (CT) scanner including an X-ray source; and
a detector for receiving X-ray radiation from the X-ray source after it passes through a sample to be imaged,
wherein the detector includes a first pair of electrodes and a second pair of electrodes disposed thereon and configured to provide a first voltage and a second voltage, respectively, to the detector.

Embodiment 2

The imaging system according to embodiment 1, wherein the detector includes a first layer and a second layer.

Embodiment 3

The imaging system according to embodiment 2, wherein the first pair of electrodes is disposed on the first layer and applies the first voltage to the first layer, and wherein the second pair of electrodes is disposed on the second layer and applies the second voltage to the second layer.

Embodiment 4

The imaging system according to any of embodiments 2-3, wherein the first layer and the second layer comprise the same material.

Embodiment 5

The imaging system according to any of embodiments 1-4, wherein the detector comprises a sensor material.

Embodiment 6

The imaging system according to any of embodiments 1-5, wherein the detector comprises at least one of cadmium zinc telluride (CZT), silicon (e.g., $p^-$, $p^+$, $n^-$, or $n^+$ silicon), and cadmium telluride (CdTe).

Embodiment 7

The imaging system according to any of embodiments 1-6, wherein the detector comprises CZT.

Embodiment 8

The imaging system according to any of embodiments 1-6, wherein the detector comprises CdTe.

Embodiment 9

The imaging system according to any of embodiments 1-6, wherein the detector comprises silicon.

Embodiment 10

The imaging system according to any of embodiments 1-6, wherein the detector comprises $p^-$, $p^+$, $n^-$, or $n^+$ silicon.

Embodiment 11

The imaging system according to any of embodiments 1-6, wherein the detector comprises $p^-$ silicon.

Embodiment 12

The imaging system according to any of embodiments 1-6, wherein the detector comprises $p^+$ silicon.

Embodiment 13

The imaging system according to any of embodiments 1-6, wherein the detector comprises $n^-$ silicon.

Embodiment 14

The imaging system according to any of embodiments 1-6, wherein the detector comprises $n^+$ silicon.

Embodiment 15

The imaging system according to any of embodiments 1-14, wherein the first voltage is equal to the second voltage.

Embodiment 16

The imaging system according to any of embodiments 1-14, wherein the first voltage is greater than the second voltage.

Embodiment 17

The imaging system according to any of embodiments 1-14, wherein the first voltage is less than the second voltage.

Embodiment 18

The imaging system according to any of embodiments 2-17, wherein the first layer and the second layer are defined by the first and second pairs of electrodes, respectively.

Embodiment 19

The imaging system according to any of embodiments 1-18, wherein both electrodes of the first pair of electrodes are disposed parallel to a direction of X-rays incoming from the X-ray source.

Embodiment 20

The imaging system according to any of embodiments 1-19, wherein both electrodes of the first pair of electrodes are disposed such that incoming X-rays from the X-ray source are first incident on a side of the detector not having any of the first pair of electrodes disposed thereon.

Embodiment 21

The imaging system according to any of embodiments 1-20, wherein both electrodes of the second pair of electrodes are disposed parallel to a direction of X-rays incoming from the X-ray source.

Embodiment 22

The imaging system according to any of embodiments 1-21, wherein both electrodes of the second pair of electrodes are disposed such that incoming X-rays from the X-ray source are second incident on a side of the detector not having any of the second pair of electrodes disposed thereon.

Embodiment 23

The imaging system according to any of embodiments 1-18 and 20-22, wherein both electrodes of the first pair of electrodes are disposed perpendicular to a direction of X-rays incoming from the X-ray source.

Embodiment 24

The imaging system according to any of embodiments 1-19 and 21-23, wherein both electrodes of the first pair of electrodes are disposed such that incoming X-rays from the X-ray source are first incident on a side of the detector having both electrodes of the first pair of electrodes disposed thereon.

Embodiment 25

The imaging system according to any of embodiments 1-20 and 22-24, wherein both electrodes of the second pair of electrodes are disposed perpendicular to a direction of X-rays incoming from the X-ray source.

Embodiment 26

The imaging system according to any of embodiments 1-21 and 23-25, wherein both electrodes of the second pair of electrodes are disposed such that incoming X-rays from the X-ray source are second incident on a side of the detector having both electrodes of the second pair of electrodes disposed thereon.

Embodiment 27

The imaging system according to any of embodiments 1-26, wherein the detector further comprises a third pair of electrodes disposed thereon and configured to provide a third voltage to the detector.

Embodiment 28

The imaging system according to embodiment 27, wherein the detector further comprises a fourth pair of electrodes disposed thereon and configured to provide a fourth voltage to the detector.

Embodiment 29

The imaging system according to any of embodiments 2-28, wherein the detector further comprises a third layer.

Embodiment 30

The imaging system according to embodiment 29, wherein the detector further comprises a fourth layer.

Embodiment 31

The imaging system according to embodiment 27, wherein the detector includes first to third layers, and wherein the first to third pairs of electrodes are disposed on and configured to provide the first to third voltages to the first to third layers, respectively.

Embodiment 32

The imaging system according to embodiment 28, wherein the detector includes first to fourth layers, and wherein the first to fourth pairs of electrodes are disposed on and configured to provide the first to fourth voltages to the first to fourth layers, respectively.

Embodiment 33

The imaging system according to embodiment 28, wherein the first to fourth voltages are all the same.

Embodiment 34

The imaging system according to embodiment 28, wherein the first to fourth voltages are all different from each other.

Embodiment 35

The imaging system according to any of embodiments 30 and 32, wherein the detector comprises the third and fourth pairs of electrodes, and wherein the first, second, third, and fourth layers are defined by the first to fourth pairs of electrodes, respectively.

Embodiment 36

The imaging system according to any of embodiments 1-35, further comprising a controller configured to control the first and second pairs of electrodes (and third and fourth pairs of electrodes, if present) to apply the first and second voltages (and the third and fourth voltages, if the third and fourth pairs of electrodes are present) such that photons in the detector are captured in a high energy bin and a low energy bin.

Embodiment 37

The imaging system according to embodiment 36, wherein the controller is configured to control the pairs of electrodes to apply the voltages such that photons in the detector are captured in the high energy bin and the low energy bin in a predetermined ratio.

Embodiment 38

The imaging system according to any of embodiments 2-37, wherein a thickness of each layer of the detector present (e.g., first layer, second layer, third layer (if present), fourth layer (if present)) is the same as that of each other layer of the detector present.

Embodiment 39

The imaging system according to any of embodiments 2-37, wherein a thickness of at least one layer of the detector present (e.g., first layer, second layer, third layer (if present), fourth layer (if present)) is different from that of at least one other layer of the detector present.

Embodiment 40

The imaging system according to any of embodiments 2-37, wherein a thickness of each layer of the detector present (e.g., first layer, second layer, third layer (if present), fourth layer (if present)) is the different from that of each other layer of the detector present.

Embodiment 41

The imaging system according to any of embodiments 1-40, further comprising a (non-transitory) machine-readable medium (e.g., a computer-readable medium) having machine-executable (e.g., computer-executable) instructions for performing an energy resolving process on the collected X-ray radiation (e.g., on collected charges of the X-ray radiation).

Embodiment 42

The imaging system according to embodiment 41, wherein the energy resolving process includes:
determining the generated charge density within the detector using Formula 1:

$$m_1 E_1 N_1 a_{k1} + m_2 E_2 N_2 a_{k2} + \ldots + m_n E_n N_n a_{kn} = g_k(x),\quad \text{Formula 1}$$

where $E_i$ is photon energy, $N_i$ is photon density with energy $E_i$, $a_{ki}$ is the attenuation coefficient of photon with energy $E_i$ for the given material thickness, $m_i$ is an empirical coefficient that represents the number of generated charges by photons with energy $E_i$ per energy unit, and $g_k(x)$ is the generated charge density within the material of the detector of a specific thickness; and
repeating the determination of the generated charge density at a different thickness within the material of the detector.

Embodiment 43

The imaging system according to any of embodiments 41-42, further comprising a processor, wherein the energy resolving process is performed by the processor.

Embodiment 44

The imaging system according to any of embodiments 1-43, configured to perform imaging on a sample that is a part of a human patient (e.g., a body part).

Embodiment 45

The imaging system according to any of embodiments 1-44, wherein the X-ray source is configured to provide X-ray radiation that has an energy of from 10 keV to 120 keV.

Embodiment 46

The imaging system according to any of embodiments 1-44, wherein the X-ray source is configured to provide X-ray radiation that has an energy of less than 20 keV.

Embodiment 47

The imaging system according to any of embodiments 1-44, wherein the X-ray source is configured to provide X-ray radiation that has an energy of more than 20 keV.

Embodiment 48

The imaging system according to any of embodiments 1-47, wherein the detector includes a fixed thresholding detector.

Embodiment 49

The imaging system according to any of embodiments 1-47, wherein the detector includes a dynamic thresholding detector.

Embodiment 50

The imaging system according to any of embodiments 1-49, wherein the CT scanner (potentially in combination with the detector) has third-generation geometry.

Embodiment 51

The imaging system according to any of embodiments 1-49, wherein the CT scanner (potentially in combination with the detector) has fourth-generation geometry.

Embodiment 52

The imaging system according to any of embodiments 1-51, further comprising an analog-digital converter (ADC) electrically connected to the detector and configured to quantify collected charges from the detector.

Embodiment 53

A method of imaging, comprising: providing the imaging system according to any of embodiments 1-52; and using the imaging system for its intended purpose to image the sample.

Embodiment 54

A method of imaging, comprising:
providing X-ray radiation to a sample to be imaged;
collecting the X-ray radiation with a detector;
providing a first voltage to the detector using a first pair of electrodes disposed thereon; and
providing a second voltage to the detector using a second pair of electrodes disposed thereon.

Embodiment 55

The method according to embodiment 54, wherein the detector includes a first layer and a second layer.

Embodiment 56

The method according to embodiment 55, wherein the first pair of electrodes is disposed on the first layer and applies the first voltage to the first layer, and wherein the second pair of electrodes is disposed on the second layer and applies the second voltage to the second layer.

Embodiment 57

The method according to any of embodiments 55-56, wherein the first layer and the second layer comprise the same material.

Embodiment 58

The method according to any of embodiments 54-57, wherein the detector comprises a sensor material.

Embodiment 59

The method according to any of embodiments 54-58, wherein the detector comprises at least one of cadmium zinc telluride (CZT), silicon (e.g., $p^-$, $p^+$, $n^-$, or $n^+$ silicon), and cadmium telluride (CdTe).

Embodiment 60

The method according to any of embodiments 54-59, wherein the detector comprises CZT.

Embodiment 61

The method according to any of embodiments 54-59, wherein the detector comprises CdTe.

Embodiment 62

The method according to any of embodiments 54-59, wherein the detector comprises silicon.

Embodiment 63

The method according to any of embodiments 54-59, wherein the detector comprises $p^-$, $p^+$, $n^-$, or $n^+$ silicon.

Embodiment 64

The method according to any of embodiments 54-59, wherein the detector comprises $p^-$ silicon.

Embodiment 65

The method according to any of embodiments 54-59, wherein the detector comprises $p^+$ silicon.

Embodiment 66

The method according to any of embodiments 54-59, wherein the detector comprises $n^-$ silicon.

Embodiment 67

The method according to any of embodiments 54-59, wherein the detector comprises $n^+$ silicon.

Embodiment 68

The method according to any of embodiments 54-67, wherein the first voltage is equal to the second voltage.

Embodiment 69

The method according to any of embodiments 54-67, wherein the first voltage is greater than the second voltage.

Embodiment 70

The method according to any of embodiments 54-67, wherein the first voltage is less than the second voltage.

Embodiment 71

The method according to any of embodiments 54-70, further comprising dynamically modulating at least one of the first voltage and the second voltage such that photons in the detector are captured in a high energy bin and a low energy bin in a predetermined ratio.

Embodiment 72

The method according to any of embodiments 54-70, further comprising dynamically modulating both the first voltage and the second voltage (and any other voltages that may be applied by additional electrode pairs that may be present) such that photons in the detector are captured in a high energy bin and a low energy bin in a predetermined ratio.

Embodiment 73

The method according to any of embodiments 71-72, wherein the ratio (higher energy bin:lower energy bin) is 2:1, 3:1, 4:1, 1:2, 1:3, 1:4, 5:1, 1:5, 1.5:1, 1:1.5, 2.5:1, 1:2.5, 3.5:1, 1:3.5, 4.5:1, or 1:4.5.

Embodiment 74

The method according to any of embodiments 54-73, further comprising dividing the X-ray spectrum into low and high energies at different proportions during detection such that detected X-ray radiation is classified as either high energy or low energy during detection by modulating the first and second voltages (and any other voltages that may be applied by additional electrode pairs that may be present).

Embodiment 75

The method according to embodiment 74, wherein the low and high energies are divided into proportions of (low/high) 10%/90%, 20%/80%, 70%/30%, 60%/40%, 50%/50%, 40%/60%, 30%, 70%, 20%/80%, and 10%/90% during detection by modulating the first and second voltages (and any other voltages that may be applied by additional electrode pairs that may be present).

Embodiment 76

The method according to any of embodiments 74-75, further comprising distributing these detector variants in a natural sequence, and repeating until a full detector ring is covered in third generation geometry.

Embodiment 77

The method according to any of embodiments 74-75, further comprising distributing these detector variants in a natural sequence, and repeating until a full detector ring is covered in fourth generation geometry.

Embodiment 78

The method according to any of embodiments 55-77, wherein the first layer and the second layer are defined by the first and second pairs of electrodes, respectively.

Embodiment 79

The method according to any of embodiments 54-78, wherein both electrodes of the first pair of electrodes are disposed parallel to a direction of X-rays incoming from the X-ray source.

Embodiment 80

The method according to any of embodiments 54-79, wherein both electrodes of the first pair of electrodes are disposed such that incoming X-rays from the X-ray source are first incident on a side of the detector not having any of the first pair of electrodes disposed thereon.

Embodiment 81

The method according to any of embodiments 54-80, wherein both electrodes of the second pair of electrodes are disposed parallel to a direction of X-rays incoming from the X-ray source.

Embodiment 82

The method according to any of embodiments 54-81, wherein both electrodes of the second pair of electrodes are disposed such that incoming X-rays from the X-ray source are second incident on a side of the detector not having any of the second pair of electrodes disposed thereon.

Embodiment 83

The method according to any of embodiments 54-78 and 79-82, wherein both electrodes of the first pair of electrodes are disposed perpendicular to a direction of X-rays incoming from the X-ray source.

Embodiment 84

The method according to any of embodiments 54-79 and 81-83, wherein both electrodes of the first pair of electrodes are disposed such that incoming X-rays from the X-ray source are first incident on a side of the detector having both electrodes of the first pair of electrodes disposed thereon.

Embodiment 85

The method according to any of embodiments 54-80 and 82-84, wherein both electrodes of the second pair of electrodes are disposed perpendicular to a direction of X-rays incoming from the X-ray source.

Embodiment 86

The method according to any of embodiments 54-81 and 83-85, wherein both electrodes of the second pair of electrodes are disposed such that incoming X-rays from the X-ray source are second incident on a side of the detector having both electrodes of the second pair of electrodes disposed thereon.

Embodiment 87

The method according to any of embodiments 54-86, wherein the detector further comprises a third pair of electrodes disposed thereon and configured to provide a third voltage to the detector.

Embodiment 88

The method according to embodiment 87, wherein the detector further comprises a fourth pair of electrodes disposed thereon and configured to provide a fourth voltage to the detector.

Embodiment 89

The method according to any of embodiments 55-88, wherein the detector further comprises a third layer.

Embodiment 90

The method according to embodiment 89, wherein the detector further comprises a fourth layer.

Embodiment 91

The method according to embodiment 87, wherein the detector includes first to third layers, and wherein the first to third pairs of electrodes are disposed on and configured to provide the first to third voltages to the first to third layers, respectively.

Embodiment 92

The method according to embodiment 88, wherein the detector includes first to fourth layers, and wherein the first to fourth pairs of electrodes are disposed on and configured to provide the first to fourth voltages to the first to fourth layers, respectively.

Embodiment 93

The method according to embodiment 88, wherein the first to fourth voltages are all the same.

Embodiment 94

The method according to embodiment 88, wherein the first to fourth voltages are all different from each other.

Embodiment 95

The method according to any of embodiments 90 and 92, wherein the detector comprises the third and fourth pairs of electrodes, and wherein the first, second, third, and fourth layers are defined by the first to fourth pairs of electrodes, respectively.

Embodiment 96

The method according to any of embodiments 54-95, further comprising controlling (e.g., using a controller) the first and second pairs of electrodes (and third and fourth pairs of electrodes, if present) to apply the first and second voltages (and the third and fourth voltages, if the third and fourth pairs of electrodes are present) such that photons in the detector are captured in a high energy bin and a low energy bin.

Embodiment 97

The method according to embodiment 96, wherein the pairs of electrodes are controlled to apply the voltages such that photons in the detector are captured in the high energy bin and the low energy bin in a predetermined ratio.

Embodiment 98

The method according to any of embodiments 55-97, wherein a thickness of each layer of the detector present (e.g., first layer, second layer, third layer (if present), fourth layer (if present)) is the same as that of each other layer of the detector present.

Embodiment 99

The method according to any of embodiments 55-97, wherein a thickness of at least one layer of the detector present (e.g., first layer, second layer, third layer (if present), fourth layer (if present)) is different from that of at least one other layer of the detector present.

Embodiment 100

The method according to any of embodiments 55-97, wherein a thickness of each layer of the detector present (e.g., first layer, second layer, third layer (if present), fourth layer (if present)) is the different from that of each other layer of the detector present.

Embodiment 101

The method according to any of embodiments 54-100, further comprising performing an energy resolving process on the collected X-ray radiation (e.g., on collected charges of the X-ray radiation).

Embodiment 102

The method according to embodiment 101, wherein the energy resolving process includes:
determining the generated charge density within the detector using Formula 1:

$$m_1 E_1 N_1 a_{k1} + m_2 E_2 N_2 a_{k2} + \ldots + m_n E_n N_n a_{kn} = g_k(x), \quad \text{Formula 1—}$$

where $E_i$ is photon energy, $N_i$ is photon density with energy $E_i$, $a_{ki}$ is the attenuation coefficient of photon with energy $E_i$ for the given material thickness, $m_i$ is an empirical coefficient that represents the number of generated charges by photons with energy $E_i$ per energy unit, and $g_k(x)$ is the generated charge density within the material of the detector of a specific thickness; and repeating the determination of the generated charge density at a different thickness within the material of the detector.

Embodiment 103

The method according to any of embodiments 101-102, wherein the energy resolving process is performed by a processor.

Embodiment 104

The method according to any of embodiments 54-103, wherein the sample to be imaged is a part of a human patient (e.g., a body part).

Embodiment 105

The method according to any of embodiments 54-104, wherein the X-ray radiation has an energy of from 10 keV to 120 keV.

Embodiment 106

The method according to any of embodiments 54-104, wherein the X-ray radiation has an energy of less than 20 keV.

Embodiment 107

The method according to any of embodiments 54-104, wherein the X-ray radiation has an energy of more than 20 keV.

Embodiment 108

The method according to any of embodiments 54-107, wherein the detector includes a fixed thresholding detector.

Embodiment 109

The method according to any of embodiments 54-107, wherein the detector includes a dynamic thresholding detector.

Embodiment 110

The method according to any of embodiments 101-109, wherein the steps of the energy resolving process are stored on a (non-transitory) machine-readable medium (e.g., a computer-readable medium).

Embodiment 111

The method according to any of embodiments 54-110, wherein the imaging is a computed tomography (CT) scan.

Embodiment 112

The method according to any of embodiments 54-111, wherein the X-ray radiation is provided by an X-ray source of a CT scanner.

Embodiment 113

The method according to embodiment 112, wherein the CT scanner (potentially in combination with the detector) has third-generation geometry.

Embodiment 114

The method according to embodiment 112, wherein the CT scanner (potentially in combination with the detector) has fourth-generation geometry.

Embodiment 115

The method according to any of embodiments 54-114, wherein the detector is placed in an edge-on fashion during imaging, such that the X-ray irradiation enters a side of a substrate of the detector.

Embodiment 116

The imaging system according to any of embodiments 1-52 or the method according to any of embodiments 53-115, wherein each electrode present is a metal electrode.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Figure 3:
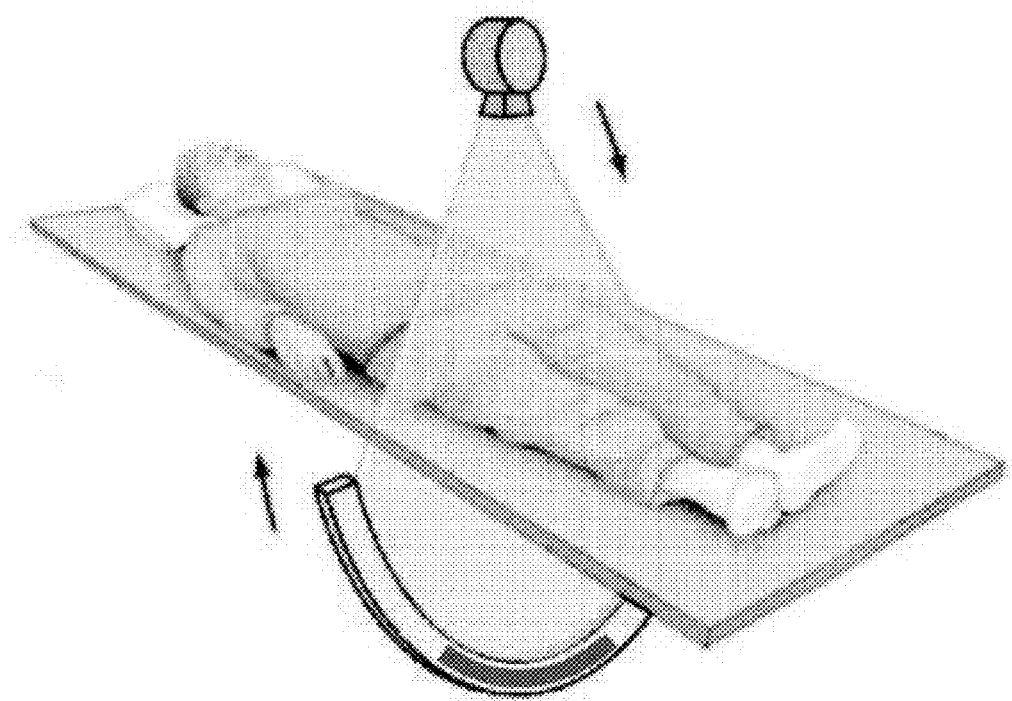
FIG. 3 shows a schematic view of direct detection of X-ray CT for third generation geometry. The detector is shown at the bottom under the human subject being imaged.
Figure 4A:
FIG. 4A shows a graphical representation of a ratio of 2:1 between number of integrating bins and number of counting bins for a numerical simulation.
Figure 4B:
FIG. 4B shows a graphical representation of a ratio of 3:1 between number of integrating bins and number of counting bins for a numerical simulation.
Figure 4C:
FIG. 4C shows a graphical representation of a ratio of 4:1 between number of integrating bins and number of counting bins for a numerical simulation.

A numerical simulation was performed using an algorithm as described by De Man et al. (An Iterative Maximum-Likelihood Polychromatic Algorithm for CT, IEEE Transactions on Medical Imaging, Vol. 20, No. 10, October 2001, which is hereby incorporated herein by reference in its entirety). The simulation was performed on a detector utilizing voltage-controlled layers as described herein. The source-to-center distance was 50 cm, the detector-to-center distance was 50 cm, the detector array width was 60 cm, the sample size was 38 by 38 cm$^2$, and the a hybrid ratio between number of integrating bins and number of counting bins was utilized, and FIGS. 4A, 4B, and 4C show graphical representations of ratios of 3:1, 4:1, and 5:1, respectively, between number of integrating bins and number of counting bins. The detection geometry was that as shown in FIG. 3.

Figure 5A:
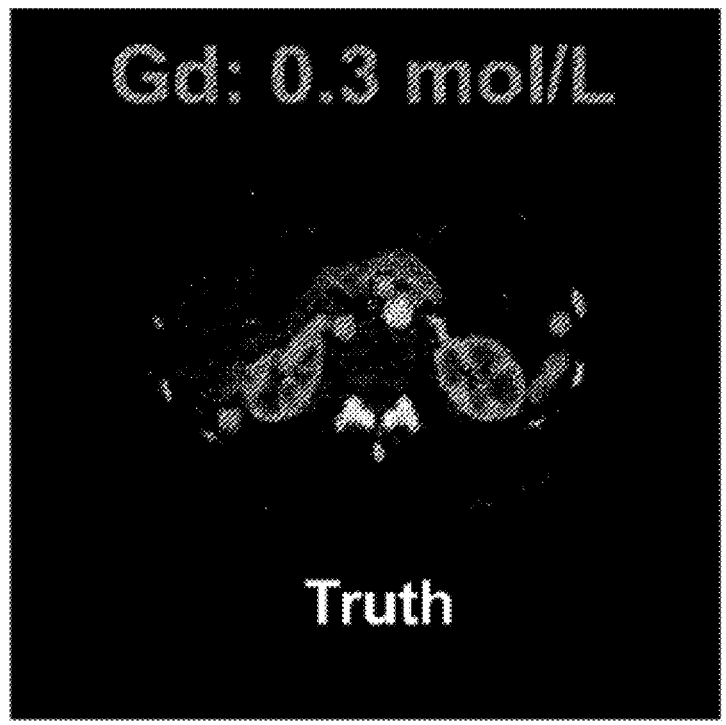
FIG. 5A shows a true image of gadolinium (Gd) contrast agent at a concentration of 0.3 mol/L.
Figure 5B:
FIG. 5B shows a reconstructed image using a ratio of 1:1 between number of integrating bins and number of counting bins for a numerical simulation.
Figure 5C:
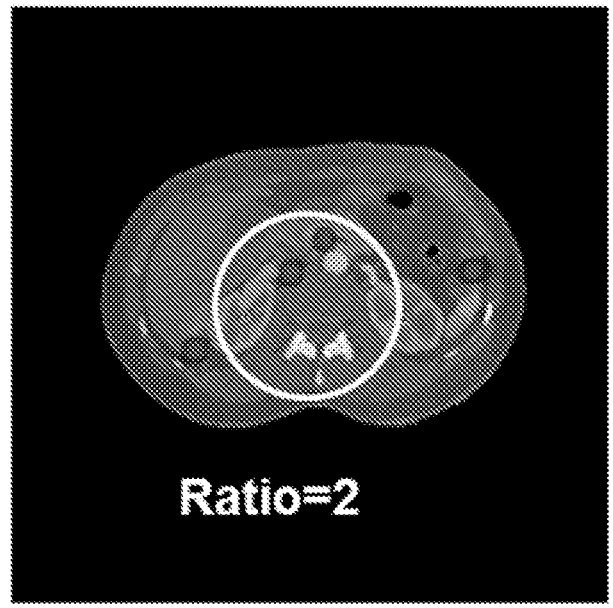
FIG. 5C shows a reconstructed image using a ratio of 2:1 between number of integrating bins and number of counting bins for a numerical simulation.
Figure 5D:
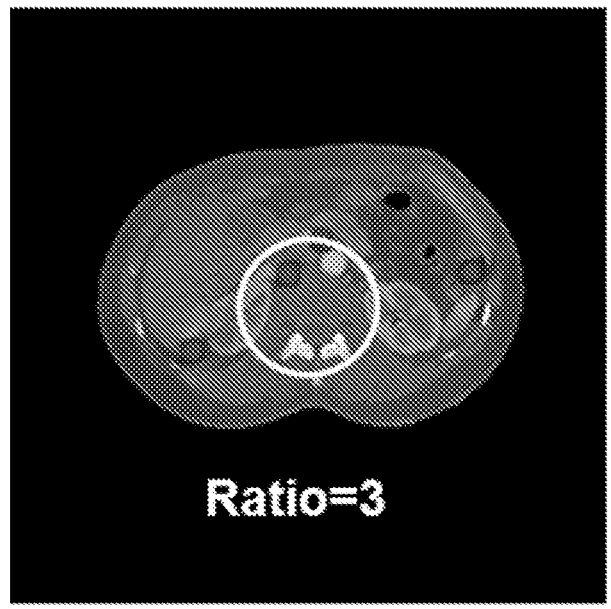
FIG. 5D shows a reconstructed image using a ratio of 3:1 between number of integrating bins and number of counting bins for a numerical simulation.

FIG. 5A shows a true image of the gadolinium (Gd) contrast agent at a concentration of 0.3 mol/L used for the simulation. FIG. 5B shows a reconstructed image using a ratio of 1:1 between number of integrating bins and number of counting bins, FIG. 5C shows a reconstructed image using a ratio of 2:1 between number of integrating bins and number of counting bins, and FIG. 5D shows a reconstructed image using a ratio of 3:1 between number of integrating bins and number of counting bins.

Example 2

A detector utilizing voltage-controlled layers as described herein was constructed, and a numerical simulation was performed to compare the detector to the Medipix 3 related art detector. The results are shown in FIG. 14. Referring to FIG. 14, the detector of the subject invention has many advantages, including shorter acquisition time, greater frame rate, and multiple working modes.

Example 3

Different configurations of dual-layer detectors according to embodiments of the subject invention were tested for performance of photon counting at varying energies of the X-ray radiation.

Figure 18A:
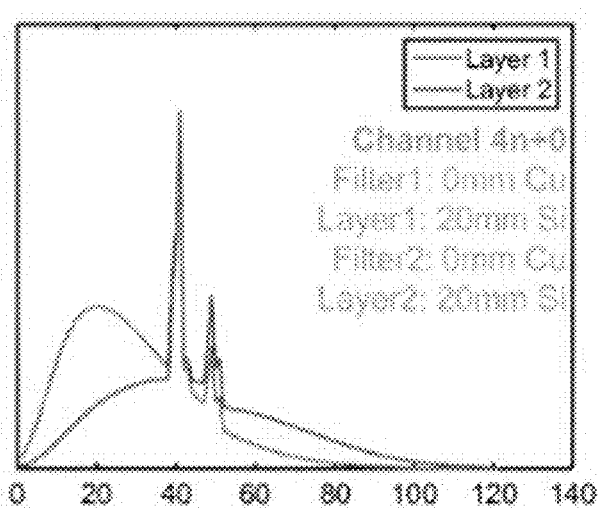
FIG. 18A shows a detection plot at varying energies for fourth generation geometry. The y-axis of the detection plot is photons/second. The first layer is closer to the X-ray source during detection, and has the higher value at lower energy in the plot.
Figure 18B:
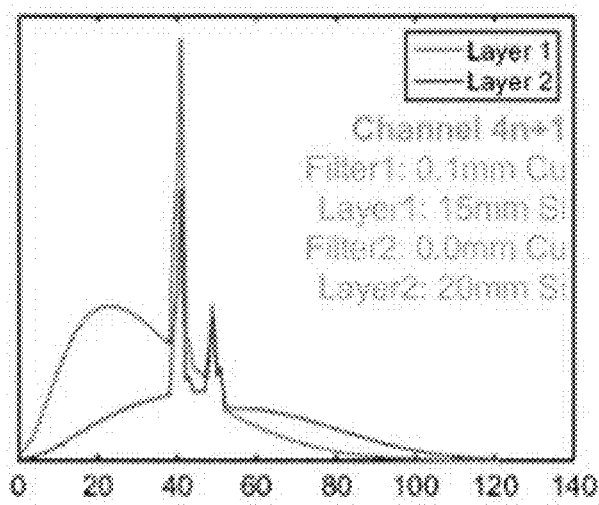
FIG. 18B shows a detection plot at varying energies for fourth generation geometry. The y-axis of the detection plot is photons/second. The first layer is closer to the X-ray source during detection, and has the higher value at lower energy in the plot.
Figure 18C:
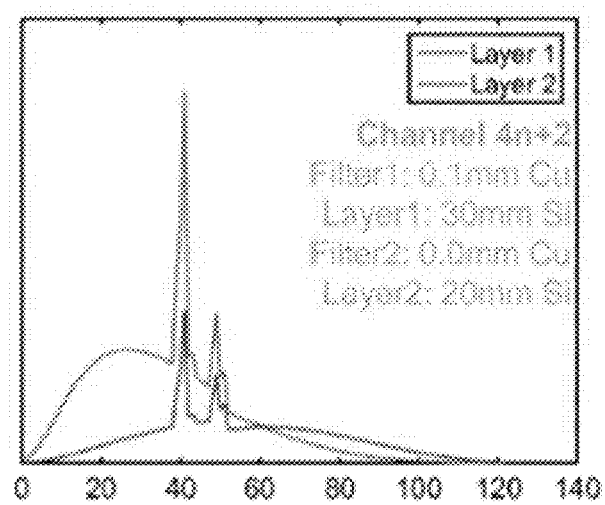
FIG. 18C shows a detection plot at varying energies for fourth generation geometry. The y-axis of the detection plot is photons/second. The first layer is closer to the X-ray source during detection, and has the higher value at lower energy in the plot.
Figure 18D:
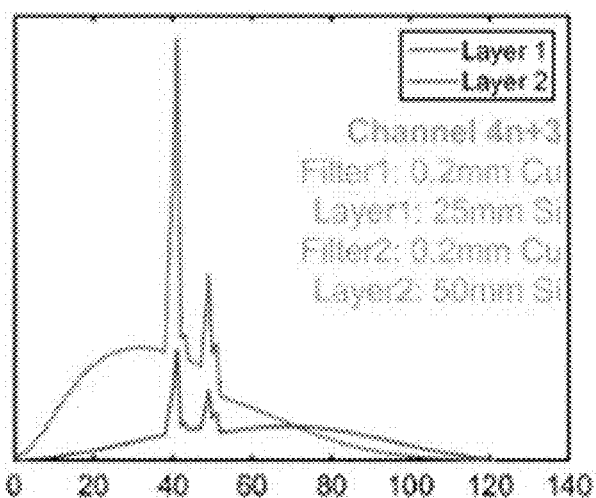
FIG. 18D shows a detection plot at varying energies for fourth generation geometry. The y-axis of the detection plot is photons/second. The first layer is closer to the X-ray source during detection, and has the higher value at lower energy in the plot.

FIG. 18A shows a detection plot for a control with channel 4n+0, a first layer of 20 mm silicon, a second layer of 20 mm silicon, and no electrodes. FIG. 18B shows a detection plot for a first variant with channel 4n+1, a first layer of 15 mm silicon, a second layer of 20 mm silicon, a first electrode pair ("Filter1") of 0.1 mm copper, and no second electrode pair ("Filter2"). FIG. 18C shows a detection plot for a second variant with channel 4n+2, a first layer of 30 mm silicon, a second layer of 20 mm silicon, a first electrode pair ("Filter1") of 0.1 mm copper, and no second electrode pair ("Filter2"). FIG. 18D shows a detection plot for a third variant with channel 4n+3, a first layer of 25 mm silicon, a second layer of 50 mm silicon, a first electrode pair ("Filter1") of 0.2 mm copper, and a second electrode pair ("Filter2") of 0.2 mm copper. In each plot, the y-axis is photons/second and the x-axis is energy (keV). In each, the first layer is closer to the X-ray source during detection, and has the higher value at lower energy in the plot. Referring to FIGS. 18A-18D, it can be seen that providing the electrodes leads to improved detection.

Example 4

A detector utilizing voltage-controlled layers as described herein was constructed and used to detect a Gd contrast agent in comparison with detection using a photon-counting detector with 10 keV spectrum resolution, four energy bins, and 1440 projections per turn.

Figure 19:
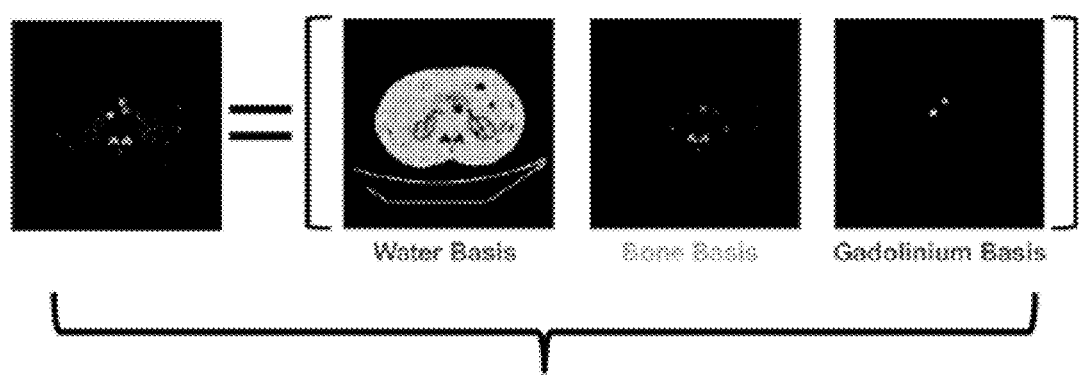
FIG. 19 shows a decomposed image of a Gd contrast agent.
Figure 20:
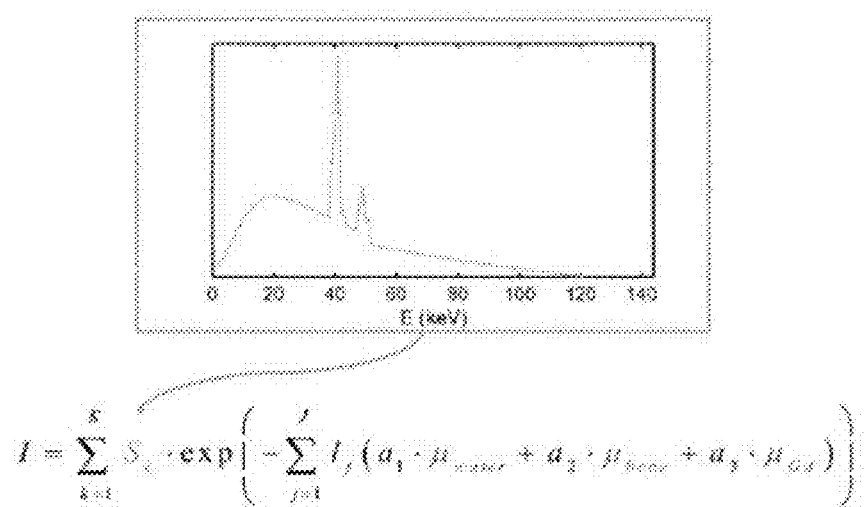
FIG. 20 shows a detection plot at varying energies based on the inset equation. The y-axis of the detection plot is photons/second.
Figure 21A:
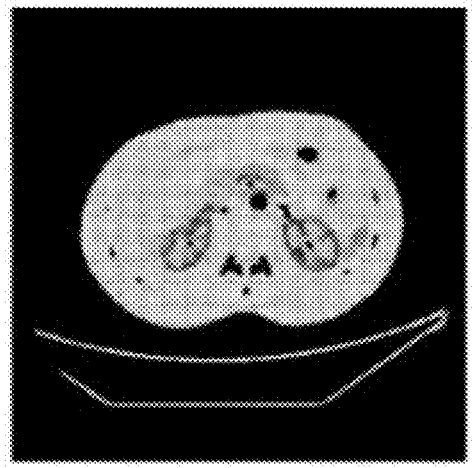
FIG. 21A shows an enlarged version of the water basis component of the image in FIG. 19.
Figure 21B:
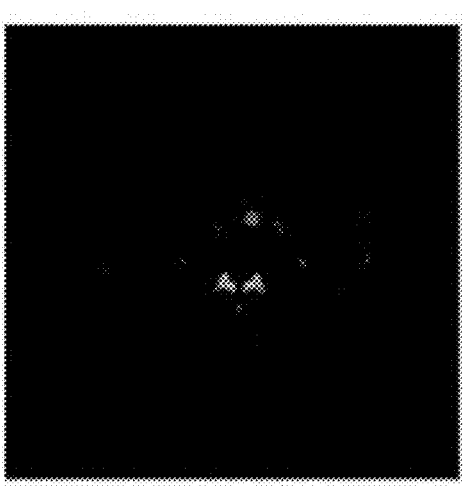
FIG. 21B shows an enlarged version of the bone basis component of the image in FIG. 19.
Figure 21C:
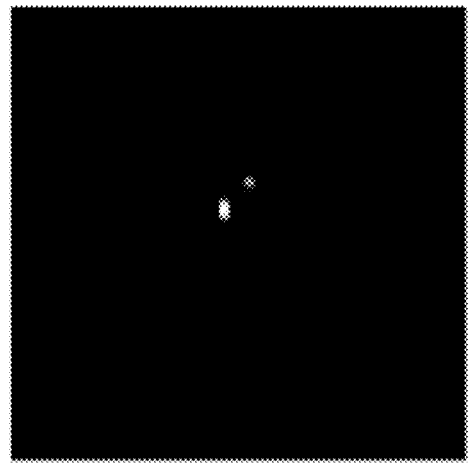
FIG. 21C shows an enlarged version of the Gd basis component of the image in FIG. 19.
Figure 22A:
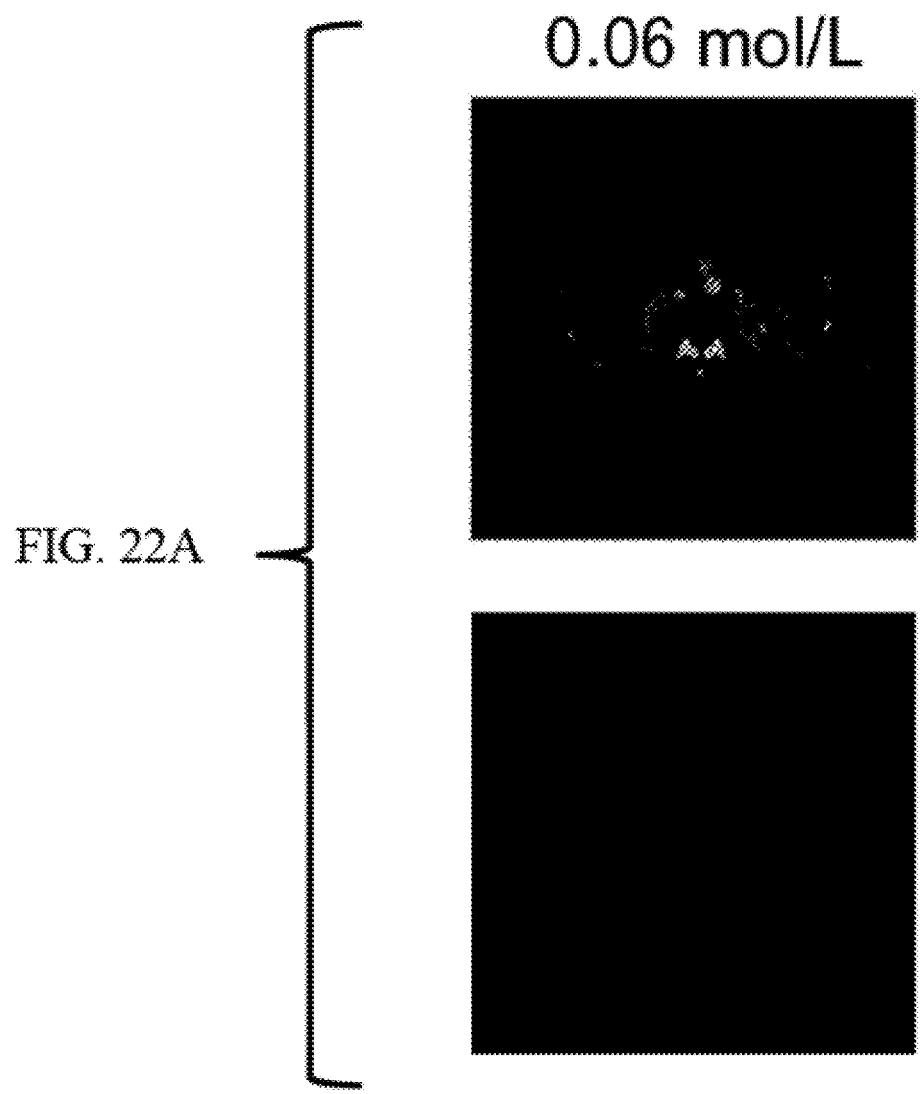
FIG. 22A shows an image of Gd contrast agent at a concentration of 0.06 mol/L (top portion) and a reconstruction of that image (bottom portion).
Figure 22B:
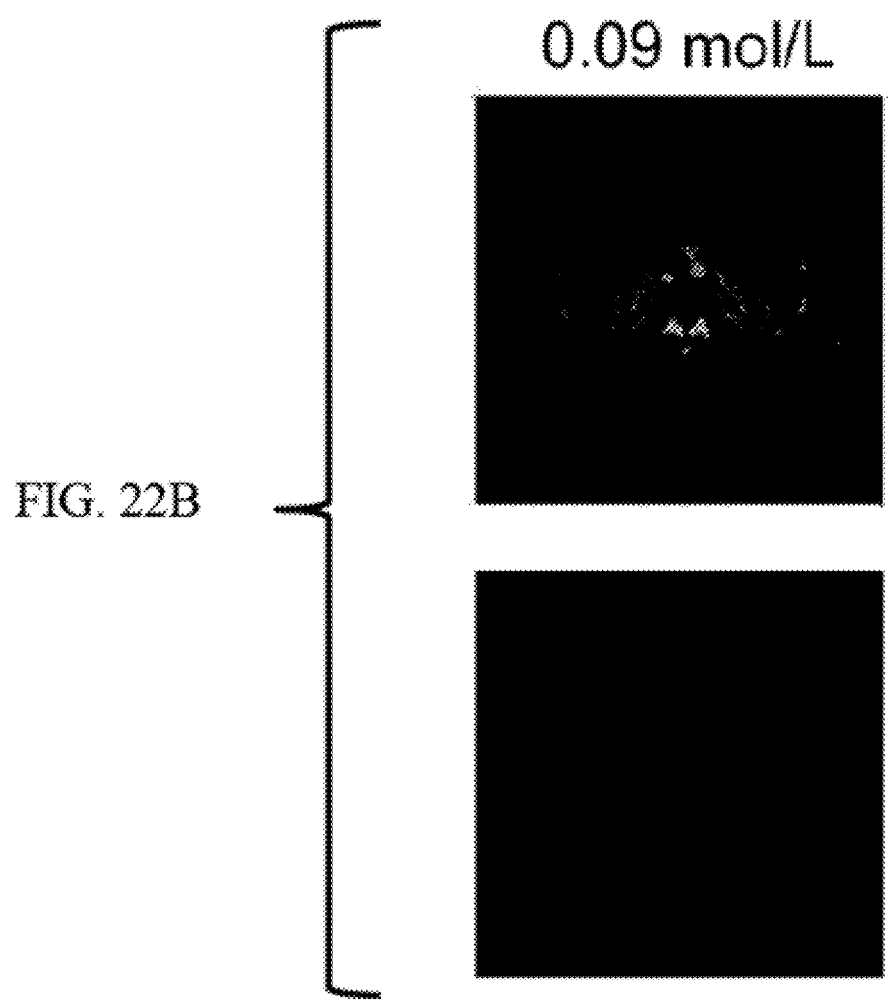
FIG. 22B shows an image of Gd contrast agent at a concentration of 0.09 mol/L (top portion) and a reconstruction of that image (bottom portion).
Figure 22C:
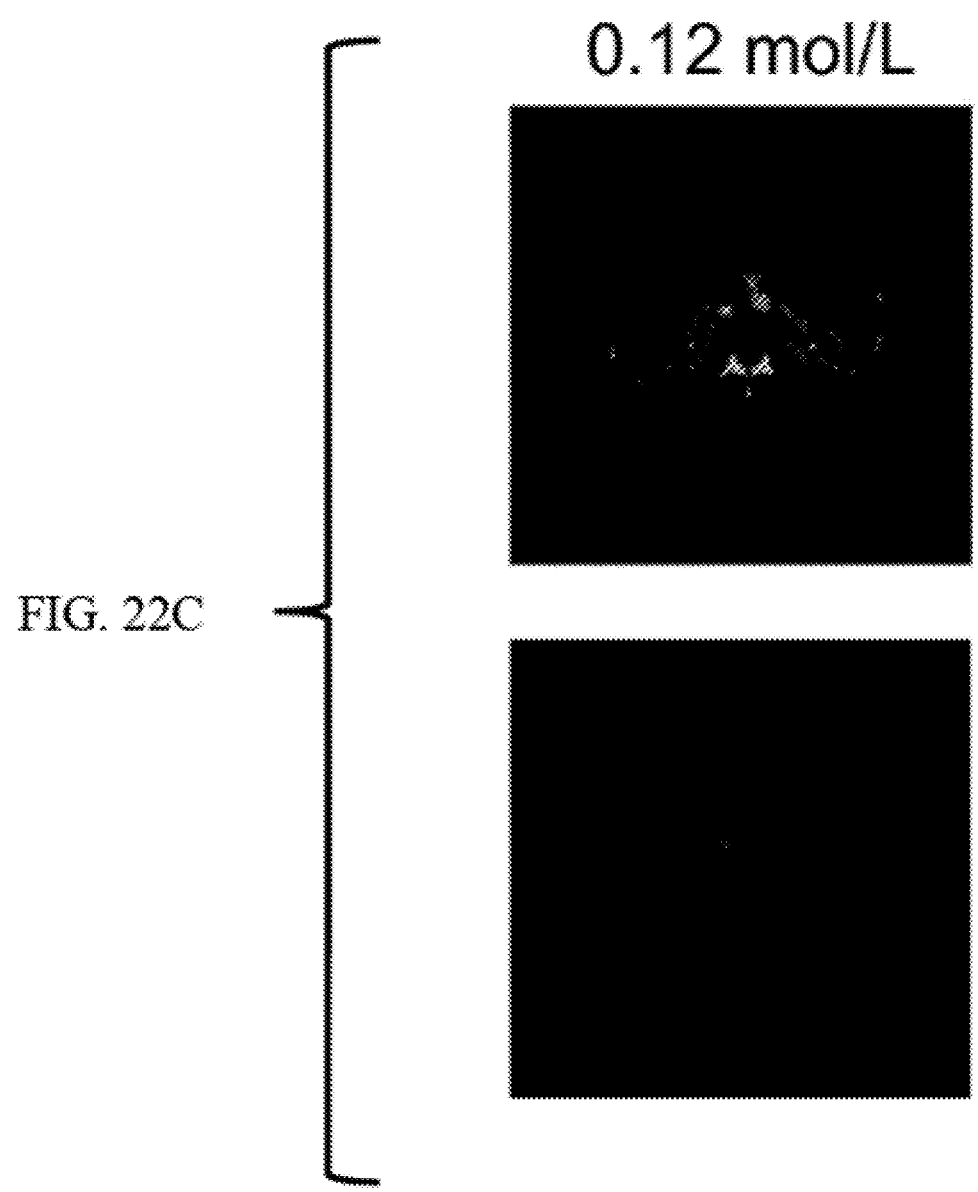
FIG. 22C shows an image of Gd contrast agent at a concentration of 0.12 mol/L (top portion) and a reconstruction of that image (bottom portion).
Figure 22D:
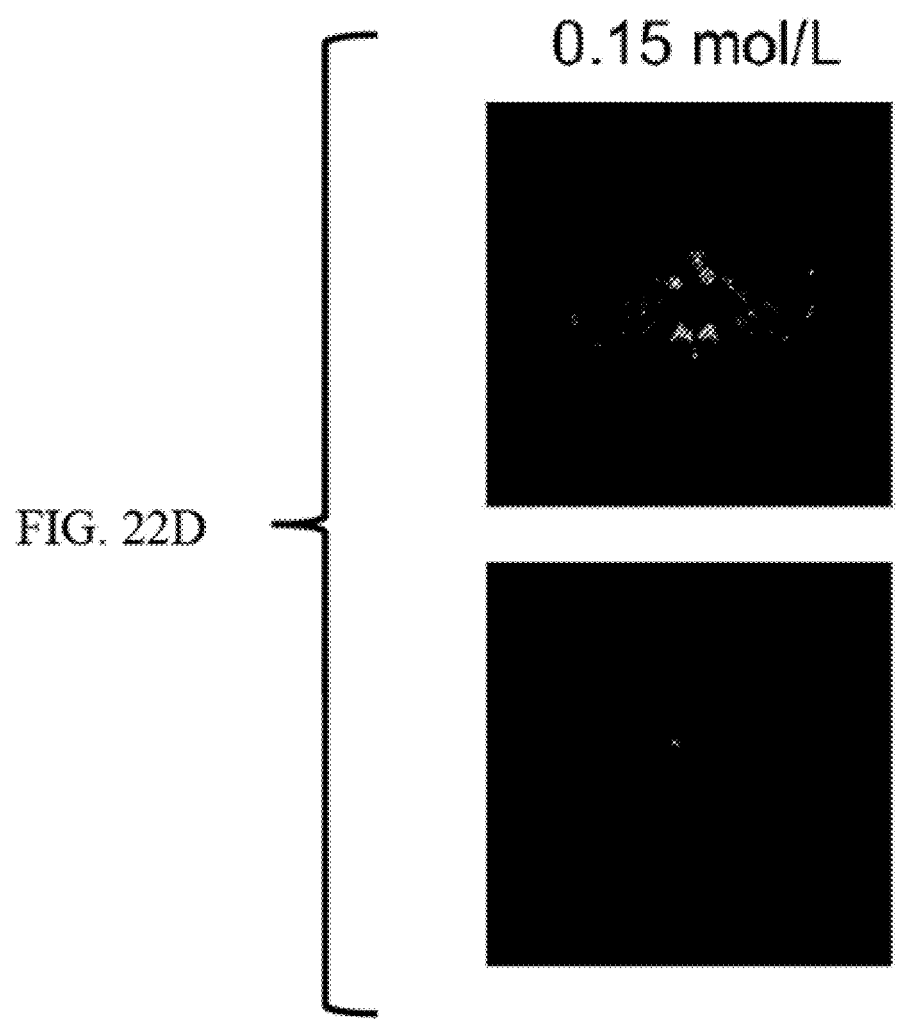
FIG. 22D shows an image of Gd contrast agent at a concentration of 0.15 mol/L (top portion) and a reconstruction of that image (bottom portion).

FIG. 19 shows a decomposed image of a Gd contrast agent. FIG. 20 shows a detection plot at varying energies based on the inset equation. The y-axis of the detection plot is photons/second. FIGS. 21A, 21B, and 21C show enlarged versions of the water basis component, the bone basis component, and the Gd basis component, respectively, of the image in FIG. 19. The image can be decomposed based on: $\mu=(a_1)(\mu_{water})$ $(a_2)(\mu_{bone})+(a_3)(\mu_{Gd})$. The image can be reconstructed using iterative maximum-likelihood and prior image constraint based on the equation at FIG. 28.

FIGS. 22A, 22B, 22C, and 22D show images of Gd contrast agent (top portion in each figure) at a concentration of 0.06 mol/L, 0.09 mol/L, 0.12 mol/L, and 0.15 mol/L, respectively, and a reconstruction of that image (bottom portion).

Figure 23:
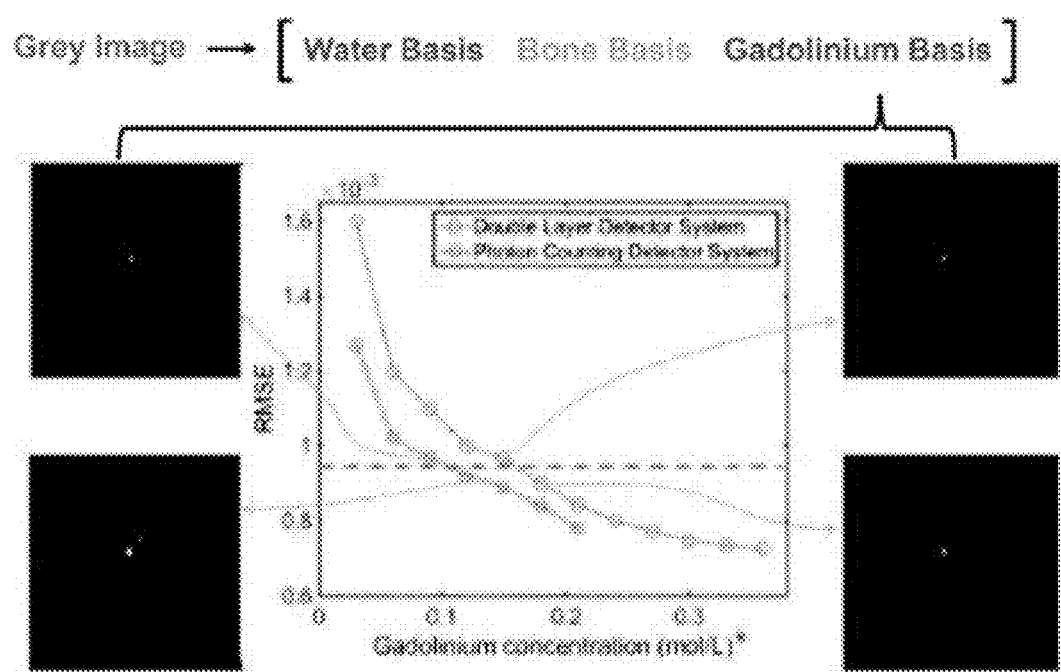
FIG. 23 shows a plot of the root mean square error (RMSE) versus Gd concentration for components of an image of Gd contrast dye.

FIG. 23 shows a detection plot at varying Gd concentration for components of an image of Gd contrast dye for both the system of the subject invention (circle data points, the line that is higher in the plot) and the photon-counting detector (square data points, the line that is lower in the plot). Referring to FIG. 23, the system of the subject invention displays good detection performance.

Example 5

Figure 24A:
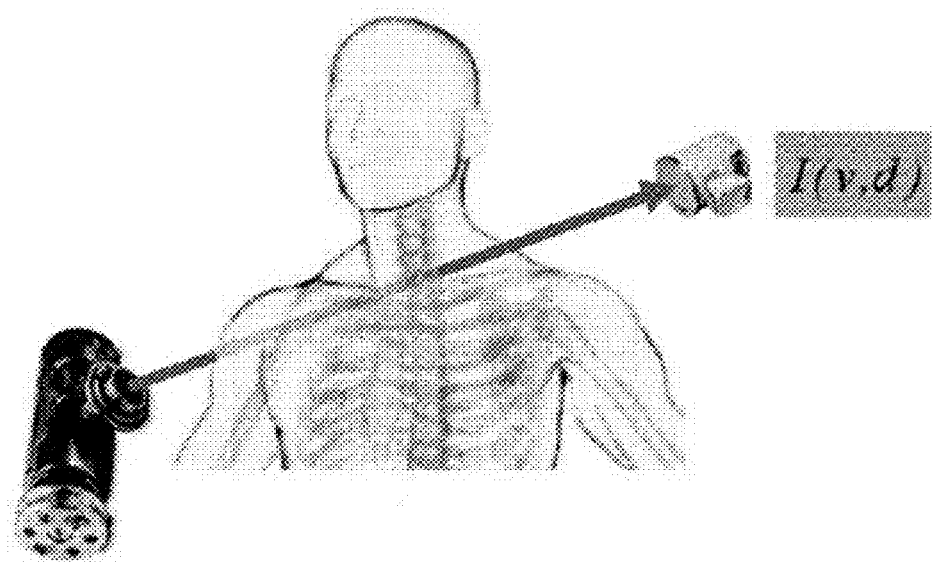
FIG. 24A shows a schematic view of a radiation source providing radiation through a human subject to a detector.
Figure 24B:
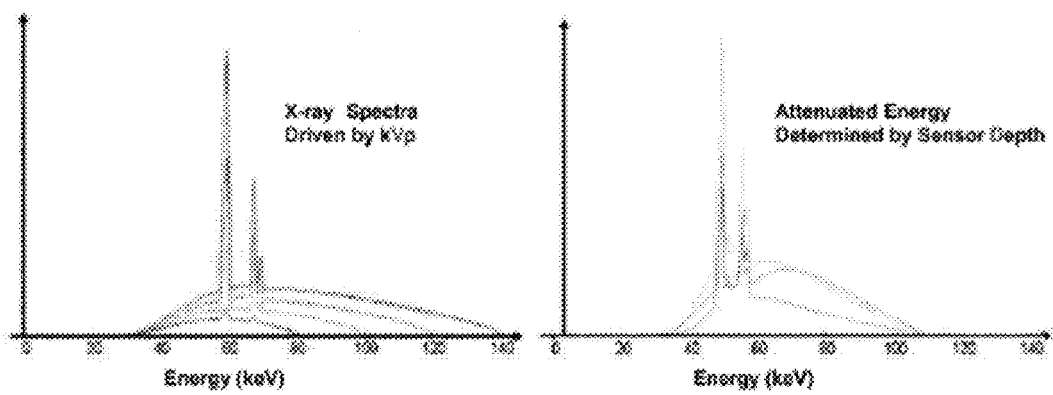
FIG. 24B shows two detection plots at varying energy. The y-axis of each detection plot is photons/second.
Figure 25:
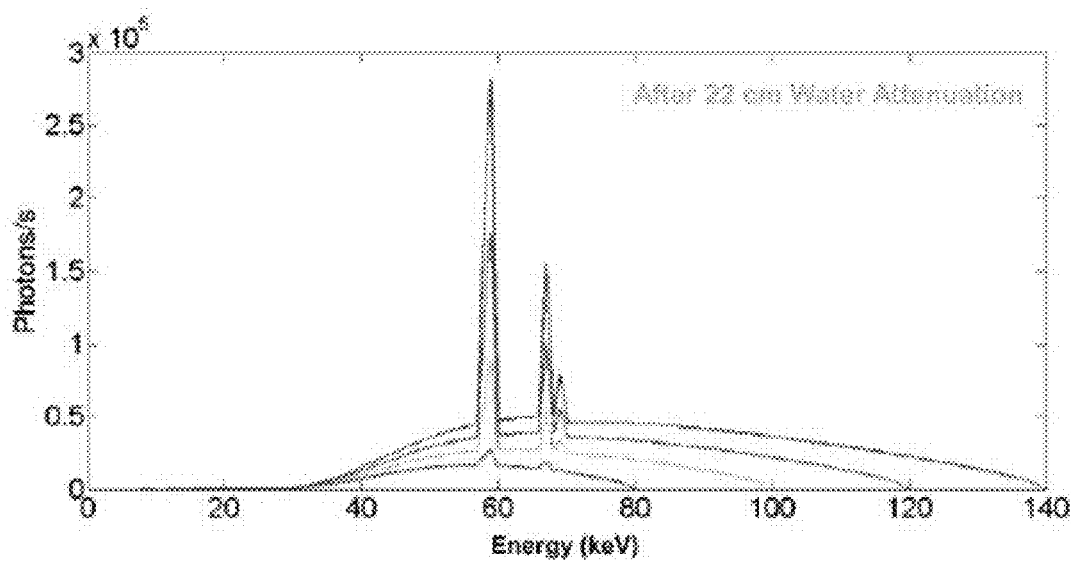
FIG. 25 shows a detection plot at varying energy after 22 cm of water attenuation.

A ray model was investigated for spectral sampling. FIG. 24A shows a schematic view of a radiation source providing radiation through a human subject to a detector, according to the ray model. FIG. 24B shows two detection plots at varying energy for the ray model. The y-axis of each detection plot is photons/second. FIG. 25 shows a detection plot of the source character at varying energy after 22 cm of water attenuation. The ray model after linearization can be summarized as shown in FIG. 29 (the lower the condition number, the better the reconstruction).

Figure 26A:
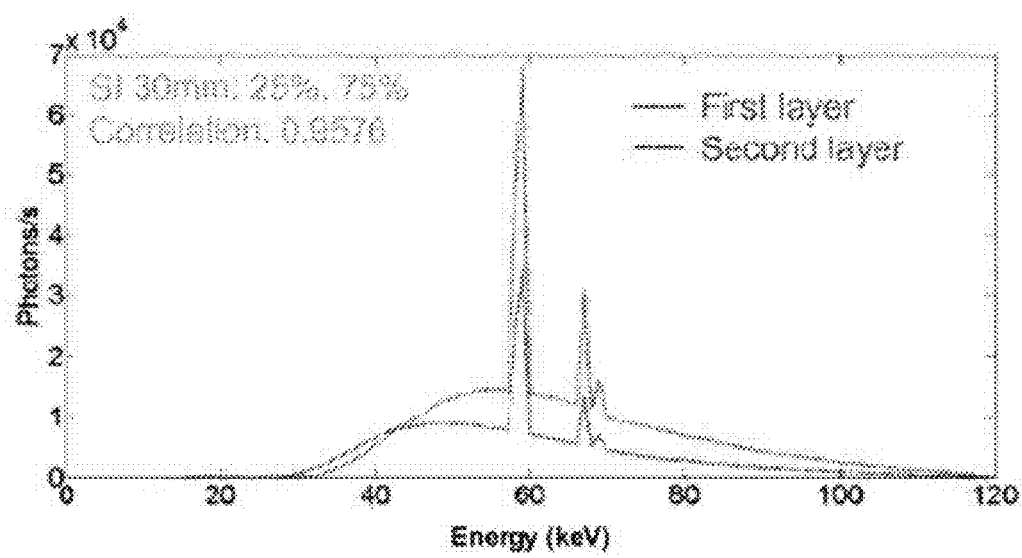
FIG. 26A shows a detection plot for first and second layers of an attenuated detector. The first layer is closer to the X-ray source during detection, and has the higher value at lower energy in the plot.
Figure 26B:
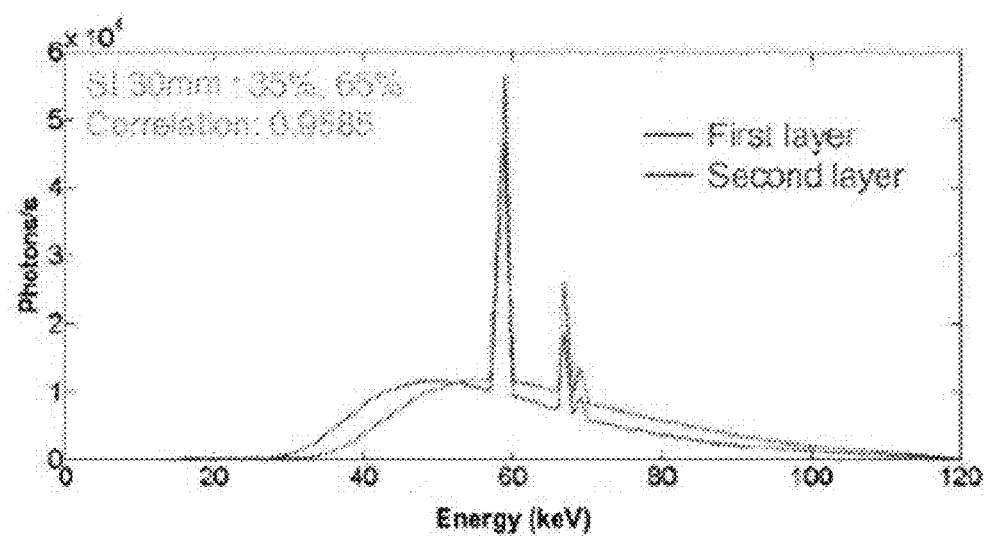
FIG. 26B shows a detection plot for first and second layers of an attenuated detector. The first layer is closer to the X-ray source during detection, and has the higher value at lower energy in the plot.
Figure 26C:
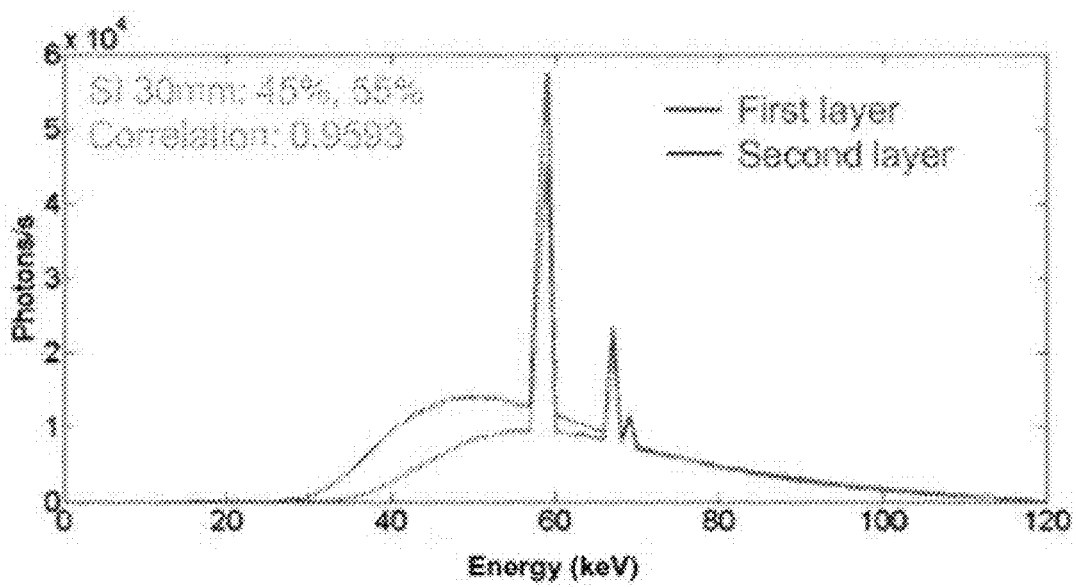
FIG. 26C shows a detection plot for first and second layers of an attenuated detector. The first layer is closer to the X-ray source during detection, and has the higher value at lower energy in the plot.
Figure 26D:
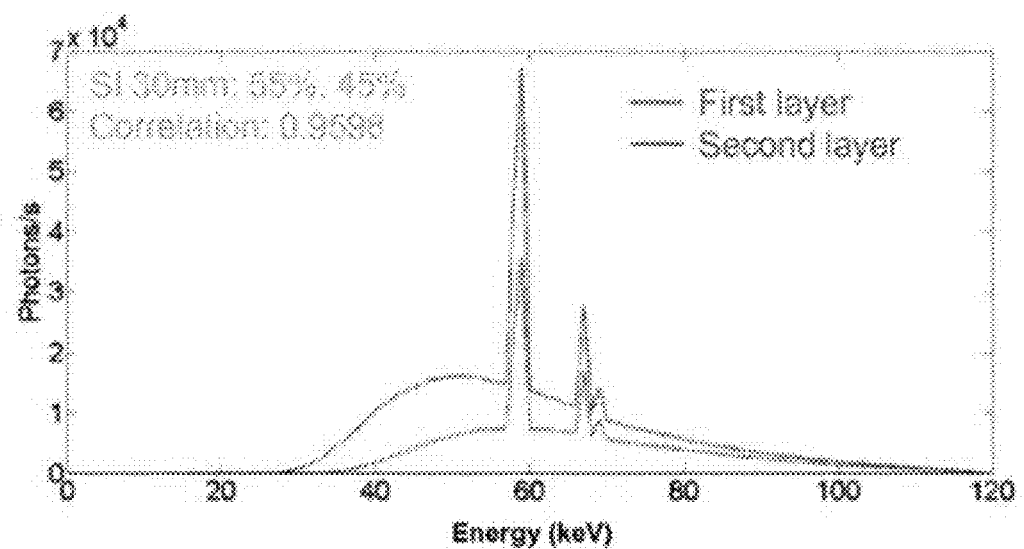
FIG. 26D shows a detection plot for first and second layers of an attenuated detector. The first layer is closer to the X-ray source during detection, and has the higher value at lower energy in the plot.

FIGS. 26A, 26B, 26C, and 26D show detection plots for first and second layers of an attenuated detector at varying percentages of first layer/entire detector substrate and second layer/entire detector substrate. In each plot, the first layer is closer to the X-ray source during detection, and has the higher value at lower energy in the plot. FIG. 26A is for a detector substrate of 30 mm silicon with percentages (first layer/entire detector substrate, second layer/entire detector substrate) of 25%, 75% and shows a correlation of 0.9576. FIG. 26B is for a detector substrate of 30 mm silicon with percentages (first layer/entire detector substrate, second layer/entire detector substrate) of 35%, 65% and shows a correlation of 0.9585. FIG. 26C is for a detector substrate of 30 mm silicon with percentages (first layer/entire detector substrate, second layer/entire detector substrate) of 45%, 55% and shows a correlation of 0.9593. FIG. 26D is for a detector substrate of 30 mm silicon with percentages (first layer/entire detector substrate, second layer/entire detector substrate) of 55%, 45% and shows a correlation of 0.9598.

Example 6

Figure 27A:
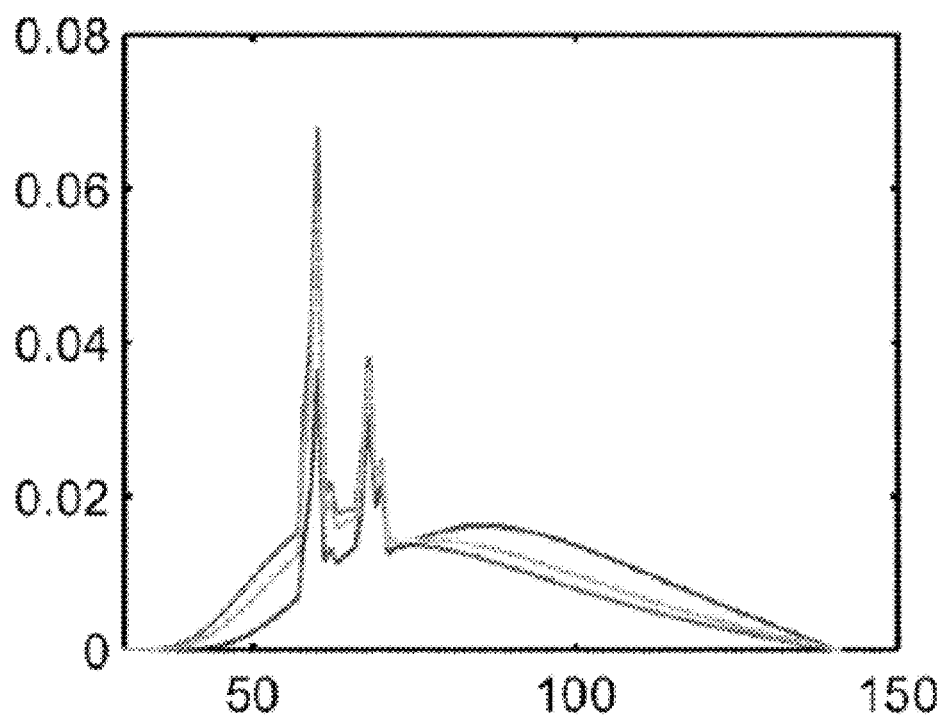
FIG. 27A shows a detection plot for first, second, and third layers in a three-layer detector.

A detector utilizing three voltage-controlled layers (triple-layer detector) as described herein was modeled using the ray model discussed in Example 5. The detector was 0.15 cm CdTe, with layer depths of 0.019 cm, 0.170 cm, and 0.052 cm. The condition number was 8.19. FIG. 27A shows a detection plot for the first, second, and third layers in this three-layer detector. This detector showed good detection performance.

Example 7

Figure 27B:
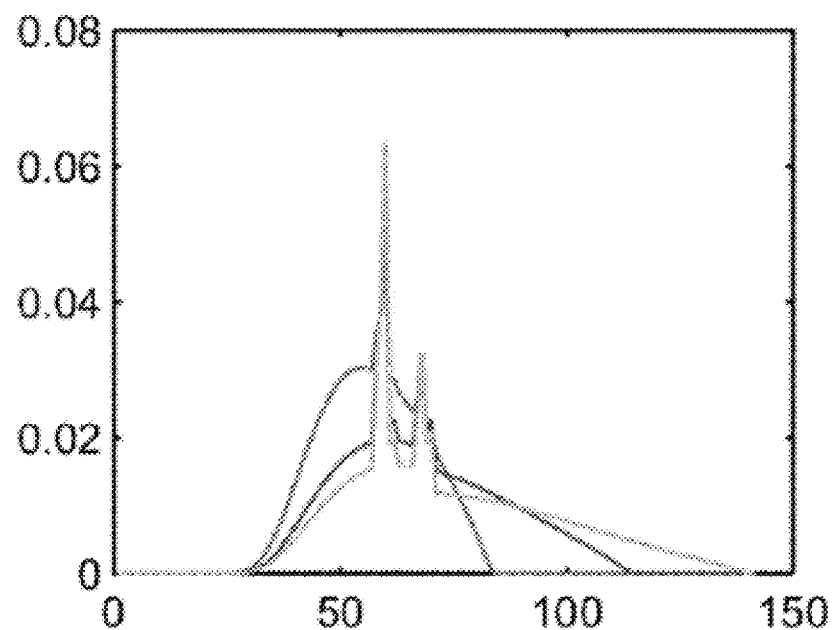
FIG. 27B shows a detection plot for first, second, and third layers in a three-layer detector.

A detector utilizing three voltage-controlled layers (triple-layer detector) as described herein was modeled using the ray model discussed in Example 5, with attenuation. The detector was 0.15 cm CdTe. The range was up to 140 keV after 30 cm of water attenuation. The best voltages were 83 kVp, 114 kVp, and 140 kVp, and the condition number was 19.72. FIG. 27B shows a detection plot for the first, second, and third layers in this three-layer detector. This detector showed good detection performance.

Example 8

Figure 27C:
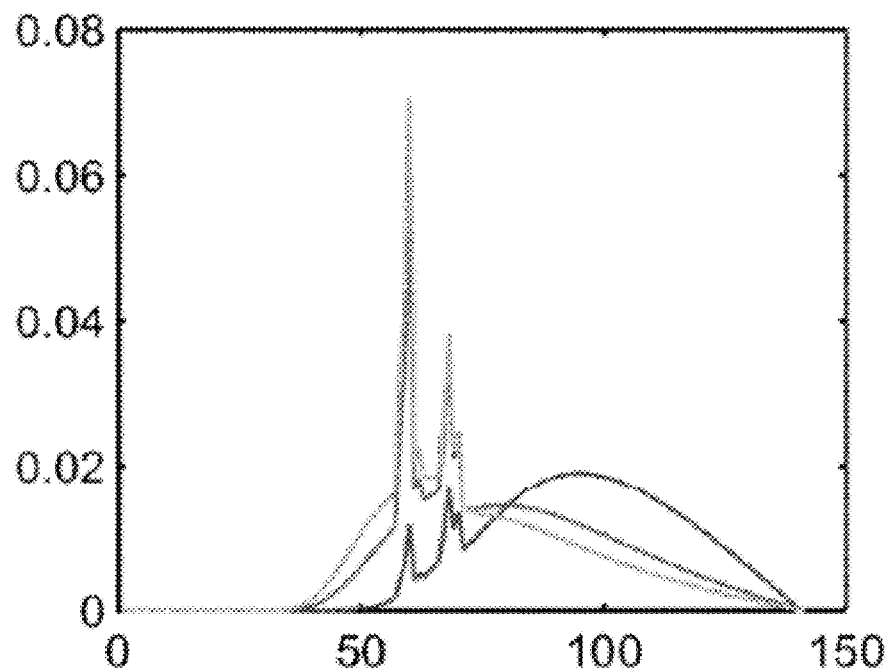
FIG. 27C shows a detection plot for first, second, and third layers in a three-layer detector.

A detector utilizing three voltage-controlled layers (triple-layer detector) as described herein was modeled using a ray model by basis materials. The detector was 0.15 cm CdTe. The ray model by basis materials can be summarized as shown in FIG. 30. The layer depths of the detector were 0.0067 cm, 0.072 cm, and 0.011 cm. The condition number was 61871. FIG. 27C shows a detection plot for the first, second, and third layers in this three-layer detector. This detector showed good detection performance.

Example 9

Figure 27D:
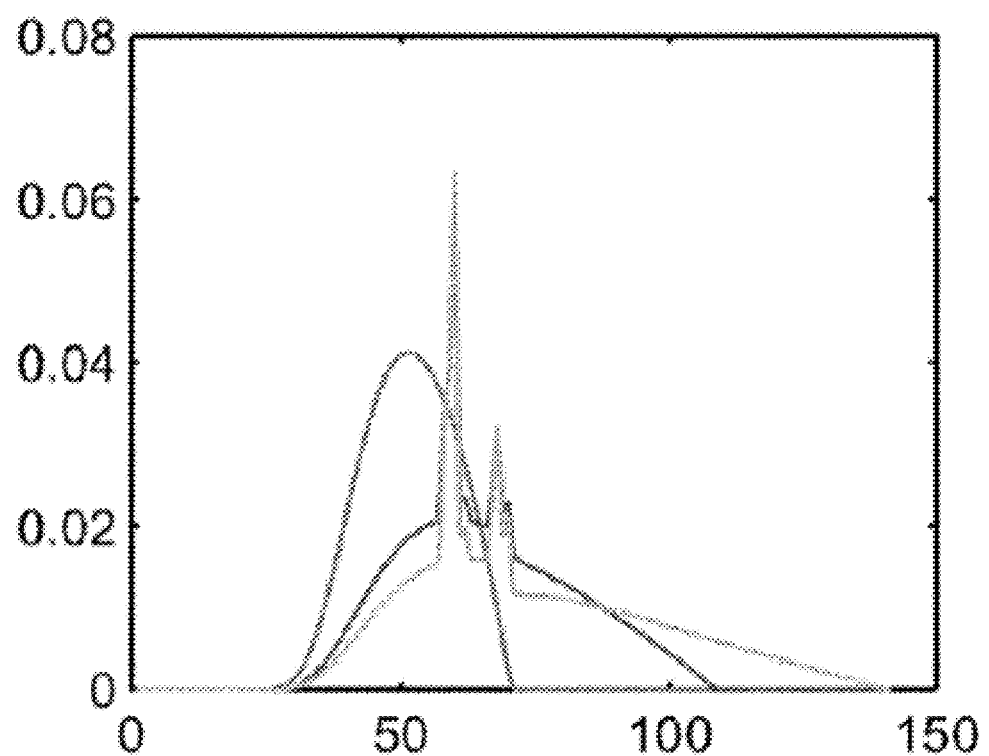
FIG. 27D shows a detection plot for first, second, and third layers in a three-layer detector.

A detector utilizing three voltage-controlled layers (triple-layer detector) as described herein was modeled using the ray model discussed in Example 8, with attenuation. The detector was 0.15 cm CdTe. The range was up to 140 keV after 30 cm of water attenuation. The best voltages were 70 kVp, 108 kVp, and 140 kVp, and the condition number was 76794. FIG. 27D shows a detection plot for the first, second, and third layers in this three-layer detector. This detector showed good detection performance.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Overdick, Michael; Baumer, Christian; Engel, K. J.; et al, "Status of Direct Conversion Detectors for Medical Imaging With X-Rays," in Nuclear Science, IEEE Transactions on, vol. 56, no. 4, pp. 1800-1809, August 2009.

Doran S J, Koerkamp K K, Bero M A, et al. A CCD-based optical CT scanner for high-resolution 3D imaging of radiation dose distributions: equipment specifications, optical simulations and preliminary results[J]. Physics in medicine and biology, 2001, 46(12): 3191.

Pan D, Roessl E, Schlomka J P, et al. Computed Tomography in Color: NanoK-Enhanced Spectral CT Molecular Imaging[J]. Angewandte Chemie, 2010, 122(50): 9829-9833.

Chu J, Cong W, Li L, et al. Combination of current-integrating/photon-counting detector modules for spectral CT[J]. Physics in medicine and biology, 2013, 58(19): 7009.

Taguchi K, Iwanczyk J S. Vision 20/20: Single photon counting x-ray detectors in medical imaging[J]. Medical physics, 2013, 40(10): 100901.

Bornefalk H, Danielsson M. Photon-counting spectral computed tomography using silicon strip detectors: a feasibility study[J]. Physics in medicine and biology, 2010, 55(7): 1999.

Persson M, Huber B, Karlsson S, et al. Energy-resolved CT imaging with a photon-counting silicon-strip detector[J]. Physics in medicine and biology, 2014, 59(22): 6709.

Gruner S M, Tate M W, Eikenberry E F. Charge-coupled device area X-ray detectors[J]. Review of Scientific Instruments, 2002, 73(8): 2815-2842.

Alvarez R E, Macovski A. Energy-selective reconstructions in x-ray computerised tomography[J]. Physics in medicine and biology, 1976, 21(5): 733.

Shikhaliev P M. Projection x-ray imaging with photon energy weighting: experimental evaluation with a prototype detector[J]. Physics in medicine and biology, 2009, 54(16): 4971.

Giersch J, Niederlohner D, Anton G. The influence of energy weighting on X-ray imaging quality[J]. Nuclear Instruments and Methods in Physics Research Section A: Accelerators, Spectrometers, Detectors and Associated Equipment, 2004, 531(1): 68-74.

Shikhaliev P M. Energy-resolved computed tomography: first experimental results[J]. Physics in medicine and biology, 2008, 53(20): 5595.

Taguchi K, Frey E C, Wang X, et al. An analytical model of the effects of pulse pileup on the energy spectrum recorded by energy resolved photon counting x-ray detectors[J]. Medical physics, 2010, 37(8): 3957-3969.

Burke, B. E.; Mountain, R. W.; Daniels, P. J.; et al, "CCD soft X-ray imaging spectrometer for the ASCA satellite," in Nuclear Science, IEEE Transactions on, vol. 41, no. 1, pp. 375-385, February 1994.

Lundqvist, M.; Cederstrom, B.; Chmill, V.; et al, "Computer simulations and performance measurements on a silicon strip detector for edge-on imaging," in Nuclear Science, IEEE Transactions on, vol. 47, no. 4, pp. 1487-1492, August 2000.

Bertolini G, Coche A. SEMICONDUCTOR DETECTORS [J]. 1968.

Marcelot, O.; Estribeau, M.; Goiffon, V.; et al, "Study of CCD Transport on CMOS Imaging Technology: Comparison Between SCCD and BCCD, and Ramp Effect on the CTI," in Electron Devices, IEEE Transactions on, vol. 61, no. 3, pp. 844-849, March 2014.

Tompsett, M. F., "Surface potential equilibration method of setting charge in charge-coupled devices," in Electron Devices, IEEE Transactions on, vol. 22, no. 6, pp. 305-309, June 1975.

Hoople, C. R.; Krusius, J. P., "Characteristics of submicrometer gaps in buried-channel CCD structures," in Electron Devices, IEEE Transactions on, vol. 38, no. 5, pp. 1175-1181, May 1991.

Arfelli, F.; Barbiellini, G.; Bonvicini, V.; et al, "An "edge-on" silicon strip detector for X-ray imaging," in Nuclear Science, IEEE Transactions on, vol. 44, no. 3, pp. 874-880, June 1997.

L. Rigon, F. Arfelli, A. Astolfo, et al. A single-photon counting "edge-on" silicon detector for synchrotron radiation mammography, Nuclear Instruments and Methods in Physics Research Section A: Accelerators, Spectrometers, Detectors and Associated Equipment, Volume 608, Issue 1, Supplement, 1 Sep. 2009, Pages S62-S65.

International Patent Application No. PCT/US2015/067441, filed Dec. 22, 2015.

U.S. Provisional Application Ser. No. 62/095,235, filed Dec. 22, 2014.

Q. Xu et al., Image Reconstruction for Hybrid True-Color Micro-CT, IEEE Transactions on Biomedical Engineering, Vol. 50, No. 6, June 2012.

B. De Man et al., An Iterative Maximum-Likelihood Polychromatic Algorithm for CT, IEEE Transactions on Medical Imaging, Vol. 20, No. 10, October 2001.

Zou, U.S. Patent Application Publication No. 2013/0251097, published Sep. 26, 2013.

D. Gierada et al., Gadolinium as a CT contrast agent: assessment in a porcine model, Radiology 210:829-834, 1999.

What is claimed is:

1. An imaging system, comprising:
a computed tomography (CT) scanner including an X-ray source; and
a detector for receiving X-ray radiation from the X-ray source after it passes through a sample to be imaged,
wherein the detector includes a first pair of electrodes and a second pair of electrodes disposed thereon and configured to provide a first voltage and a second voltage, respectively, to the detector,
wherein both electrodes of the first pair of electrodes are disposed such that incoming X-rays from the X-ray source are first incident on a side of the detector not having any of the first pair of electrodes disposed thereon, and
wherein both electrodes of the second pair of electrodes are disposed such that incoming X-rays from the X-ray source are second incident on a side of the detector not having any of the second pair of electrodes disposed thereon.

2. The imaging system according to claim 1, wherein detector includes a first layer and a second layer,
wherein the first pair of electrodes is disposed on the first layer and applies the first voltage to the first layer, and
wherein the second pair of electrodes is disposed on the second layer and applies the second voltage to the second layer, and
wherein the first voltage is different from the second voltage.

3. The imaging system according to claim 2, wherein the detector further comprises:
a third pair of electrodes disposed thereon and configured to provide a third voltage to the detector;
a fourth pair of electrodes disposed thereon and configured to provide a fourth voltage to the detector;
a third layer; and
a fourth layer,
wherein the first to fourth pairs of electrodes are disposed on and configured to provide the first to fourth voltages to the first to fourth layers, respectively, and
wherein at least one of the first to fourth voltages is different from at least one of the other voltages of the first to fourth voltages.

4. The imaging system according to claim 1, wherein the detector comprises at least one of material selected from cadmium zinc telluride (CZT), silicon, and cadmium telluride (CdTe).

5. The imaging system according to claim 1, further comprising a controller configured to control the first and second pairs of electrodes to apply the first and second voltages such that photons in the detector are captured in a high energy bin and a low energy bin, and
wherein the controller is configured to control the pairs of electrodes to apply the voltages such that photons in the detector are captured in the high energy bin and the low energy bin in a predetermined ratio.

6. The imaging system according to claim 1, further comprising:
a machine-readable medium having machine-executable instructions for performing an energy resolving process on the collected X-ray radiation; and
a processor, wherein the energy resolving process is performed by the processor, and wherein the energy resolving process comprises:
determining the generated charge density within the detector using Formula 1:

$$m_1 E_1 N_1 a_{k1} + m_2 E_2 N_2 a_{k2} + \ldots + m_n E_n N_n a_{kn} = g_k(x), \quad \text{Formula 1}$$

where $E_i$ is photon energy, $N_i$ is photon density with energy $E_i$, $a_{ki}$ is the attenuation coefficient of photon with energy $E_i$ for the given material thickness, mi is an empirical coefficient that represents the number of generated charges by photons with energy $E_i$ per energy unit, and $g_k(x)$ is the generated charge density within the material of the detector of a specific thickness; and
repeating the determination of the generated charge density at a different thickness within the material of the detector.

7. The imaging system according to claim 1, wherein the X-ray source is configured to provide X-ray radiation that has an energy of from 10 keV to 120 keV.

8. The imaging system according to claim 1, wherein the CT scanner has third-generation geometry or fourth-generation geometry.

9. A method of imaging, comprising:
providing X-ray radiation to a sample to be imaged;
collecting the X-ray radiation with a detector;
providing a first voltage to the detector using a first pair of electrodes disposed thereon; and
providing a second voltage to the detector using a second pair of electrodes disposed thereon,
wherein both electrodes of the first pair of electrodes are disposed such that incoming X-rays from the X-ray source are first incident on a side of the detector not having any of the first pair of electrodes disposed thereon, and wherein both electrodes of the second pair of electrodes are disposed such that incoming X-rays from the X-ray source are second incident on a side of the detector not having any of the second pair of electrodes disposed thereon.

10. The method according to claim 9, wherein the detector includes a first layer and a second layer,
wherein the first pair of electrodes is disposed on the first layer and applies the first voltage to the first layer,
wherein the second pair of electrodes is disposed on the second layer and applies the second voltage to the second layer, and
wherein the first voltage is different from the second voltage.

11. The method according to claim 9, wherein the detector comprises at least one of material selected from cadmium zinc telluride (CZT), silicon, and cadmium telluride (CdTe).

12. The method according to claim 9, further comprising dynamically modulating at least one of the first voltage and the second voltage such that photons in the detector are captured in a high energy bin and a low energy bin in a predetermined ratio.

13. The method according to claim 9, wherein the detector further comprises:
a third pair of electrodes disposed thereon and configured to provide a third voltage to the detector;
a fourth pair of electrodes disposed thereon and configured to provide a fourth voltage to the detector;
a third layer; and
a fourth layer,
wherein the first to fourth pairs of electrodes are disposed on and configured to provide the first to fourth voltages to the first to fourth layers, respectively, and
wherein both electrodes of the second pair of electrodes are disposed such that incoming X-rays from the X-ray source are second incident on a side of the detector not having any of the second pair of electrodes disposed thereon.

14. The method according to claim 9, further comprising controlling the first and second pairs of electrodes to apply the first and second voltages such that photons in the detector are captured in a high energy bin and a low energy bin.

15. The method according to claim 9, further comprising performing an energy resolving process on the collected X-ray radiation,
wherein the energy resolving process includes:
determining the generated charge density within the detector using Formula 1:

$$m_1 E_1 N_1 a_{k1} + m_2 E_2 N_2 a_{k2} + \ldots + m_n E_n N_n a_{kn} = g_k(x),\qquad \text{Formula 1—}$$

where $E_i$ is photon energy, $N_i$ is photon density with energy $E_i$, $a_{ki}$ is the attenuation coefficient of photon with energy $E_i$ for the given material thickness, mi is an empirical coefficient that represents the number of generated charges by photons with energy $E_i$ per energy unit, and $g_k(x)$ is the generated charge density within the material of the detector of a specific thickness; and
repeating the determination of the generated charge density at a different thickness within the material of the detector.

16. The method according to claim 9, wherein the X-ray radiation has an energy of from 10 keV to 120 keV.

17. The method according to claim 9, wherein the imaging is a computed tomography (CT) scan,
wherein the X-ray radiation is provided by an X-ray source of a CT scanner, and
wherein the CT scanner has third-generation geometry or fourth-generation geometry.

18. The method according to claim 9, wherein the detector is placed in an edge-on fashion during imaging, such that the X-ray irradiation enters a side of a substrate of the detector.

19. An imaging system, comprising:
a computed tomography (CT) scanner including an X-ray source;
a detector for receiving X-ray radiation from the X-ray source after it passes through a sample to be imaged, and
a controller configured to control the first and second pairs of electrodes to apply the first and second voltages such that photons in the detector are captured in a high energy bin and a low energy bin,
wherein the detector includes a first pair of electrodes and a second pair of electrodes disposed thereon and configured to provide a first voltage and a second voltage, respectively, to the detector, and
wherein the controller is configured to control the pairs of electrodes to apply the voltages such that photons in the detector are captured in the high energy bin and the low energy bin in a predetermined ratio.

\* \* \* \* \*